(12) United States Patent
Fujii et al.

(10) Patent No.: US 8,965,072 B2
(45) Date of Patent: Feb. 24, 2015

(54) IMAGE DISPLAY APPARATUS AND IMAGE DISPLAY SYSTEM

(75) Inventors: Kouki Fujii, Nasushiobara (JP); Masakazu Osada, Tokyo (JP); Kenichi Niwa, Otawara (JP); Shinichi Hori, Izumisano (JP); Yoshiaki Nakagawa, Izumisano (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 844 days.

(21) Appl. No.: 12/360,210

(22) Filed: Jan. 27, 2009

(65) Prior Publication Data

US 2009/0196473 A1  Aug. 6, 2009

(30) Foreign Application Priority Data

Jan. 31, 2008  (JP) ................. 2008-021492

(51) Int. Cl.
| | |
|---|---|
| G06K 9/00 | (2006.01) |
| G06F 19/00 | (2011.01) |
| A61B 6/12 | (2006.01) |
| A61B 6/00 | (2006.01) |
| G06T 5/50 | (2006.01) |
| G06T 7/00 | (2006.01) |

(52) U.S. Cl.
CPC ............. *G06F 19/3406* (2013.01); *A61B 6/12* (2013.01); *A61B 6/481* (2013.01); *A61B 6/504* (2013.01); *G06F 19/321* (2013.01); *G06T 5/50* (2013.01); *G06T 7/0012* (2013.01); *A61B 6/5235* (2013.01); *G06T 2207/10121* (2013.01); *G06T 2207/20221* (2013.01); *G06T 2207/30021* (2013.01)
USPC .......................................... 382/128; 382/100

(58) Field of Classification Search
None
See application file for complete search history.

(56) References Cited

U.S. PATENT DOCUMENTS 5,369,678 A * 11/1994 Chiu et al. ....................... 378/62
5,924,989 A *  7/1999 Polz ............................. 600/443

(Continued)

FOREIGN PATENT DOCUMENTS

| CN | 1839408 A | 9/2006 |
|---|---|---|
| JP | 5-84248 | 4/1993 |

(Continued)

OTHER PUBLICATIONS

Rhode et al ("A System for Real-Time XMR Guided Cardiovascular Intervention", 2005).*

(Continued)

*Primary Examiner* — Avinash J Yentrapati
(74) *Attorney, Agent, or Firm* — Oblon, Spivak, McClelland, Maier & Neustadt, L.L.P.

(57) ABSTRACT

A storage unit stores data of a plurality of previous images of a plurality of regions generated during a previous catheter procedure. A route map generating unit arranges a plurality of first catheter images or blood vessel images included in the plurality of previous images according to the positional relationship between the plurality of regions to generate a route map indicating the distribution of the plurality of first catheter images or blood vessel images. A specifying unit specifies a specific portion of a second catheter image included in a current image generated during a current catheter procedure. A calculating unit calculates the position of the specified specific portion on the route map on the basis of the positional relationship between the current image and the previous image. A display unit displays a specific previous image corresponding to the calculated position.

15 Claims, 17 Drawing Sheets

(56) References Cited

U.S. PATENT DOCUMENTS

| | | | |
|---|---|---|---|
| 6,246,898 B1* | 6/2001 | Vesely et al. | 600/424 |
| 6,370,417 B1* | 4/2002 | Horbaschek et al. | 600/424 |
| 7,317,819 B2* | 1/2008 | Janes | 382/128 |
| 8,031,922 B2* | 10/2011 | Haimerl et al. | 382/128 |
| 2002/0141255 A1* | 10/2002 | Inoue | 365/200 |
| 2003/0016853 A1* | 1/2003 | Oosawa | 382/132 |
| 2004/0034300 A1* | 2/2004 | Verard et al. | 600/424 |
| 2004/0086175 A1* | 5/2004 | Parker et al. | 382/154 |
| 2005/0008209 A1* | 1/2005 | Matsumoto | 382/128 |
| 2005/0020902 A1* | 1/2005 | Janes | 600/407 |
| 2005/0245807 A1* | 11/2005 | Boese et al. | 600/407 |
| 2006/0120581 A1* | 6/2006 | Eck et al. | 382/128 |
| 2006/0251300 A1* | 11/2006 | Borgert et al. | 382/128 |
| 2006/0257006 A1* | 11/2006 | Bredno et al. | 382/128 |
| 2006/0262966 A1* | 11/2006 | Eck et al. | 382/128 |
| 2007/0036410 A1* | 2/2007 | Ida et al. | 382/128 |
| 2007/0147707 A1* | 6/2007 | Coste-Maniere et al. | 382/298 |
| 2008/0175463 A1* | 7/2008 | Strommer et al. | 382/131 |
| 2008/0247503 A1* | 10/2008 | Lauritsch et al. | 378/4 |
| 2008/0287781 A1* | 11/2008 | Revie et al. | 600/426 |
| 2010/0049038 A1* | 2/2010 | Florent et al. | 600/425 |
| 2010/0094124 A1* | 4/2010 | Schoonenberg et al. | 600/424 |
| 2010/0215225 A1* | 8/2010 | Kadomura et al. | 382/128 |
| 2010/0239140 A1* | 9/2010 | Ruijters et al. | 382/130 |

FOREIGN PATENT DOCUMENTS

| | | | | |
|---|---|---|---|---|
| JP | 2000-342565 | | 12/2000 | |
| JP | WO2006/118100 | * | 11/2006 | A61B 6/03 |
| WO | WO 2004/034329 A2 | | 4/2004 | |
| WO | WO 2005/024729 | * | 3/2005 | G06T 17/00 |

OTHER PUBLICATIONS

Baert et al ("Guide Wire Tracking During Endovascular Interventions", 2003).*

Office Action issued Sep. 26, 2010, in Chinese Patent Application No. 200910009834.8, (with English translation).

Office Action issued Jun. 26, 2012, in Japanese Patent Application No. 2008-021492 with English translation.

Office Action issued Sep. 25, 2012 in Chinese Patent Application No. 200910009834.8 (with English Translation).

* cited by examiner

FIG. 2
BEFORE CURRENT IVR PROCEDURE
(1) GENERATION OF ROUTE MAP
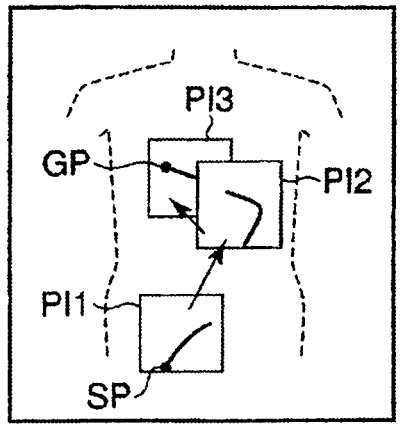
⬇
(2) COMPLETION OF ROUTE MAP
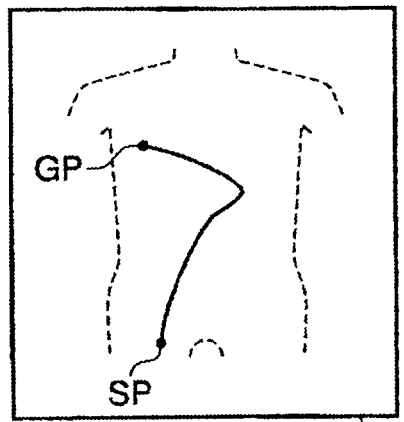
DURING CURRENT IVR PROCEDURE
(3) GENERATION OF CURRENT IMAGE CI
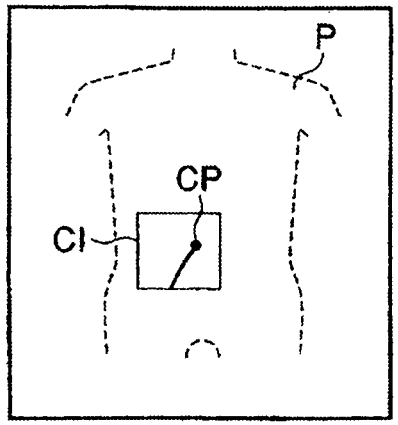
⬇
(4) SELECTION OF PREVIOUS IMAGE CORRESPONDING TO POSITION OF LEADING END OF CATHETER
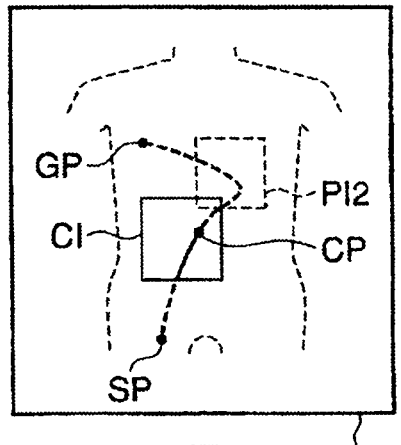
⬇
(5) DISPLAY OF PREVIOUS IMAGE
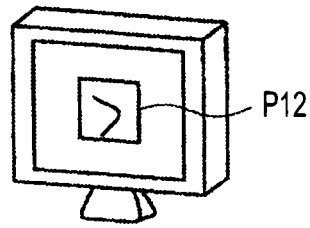

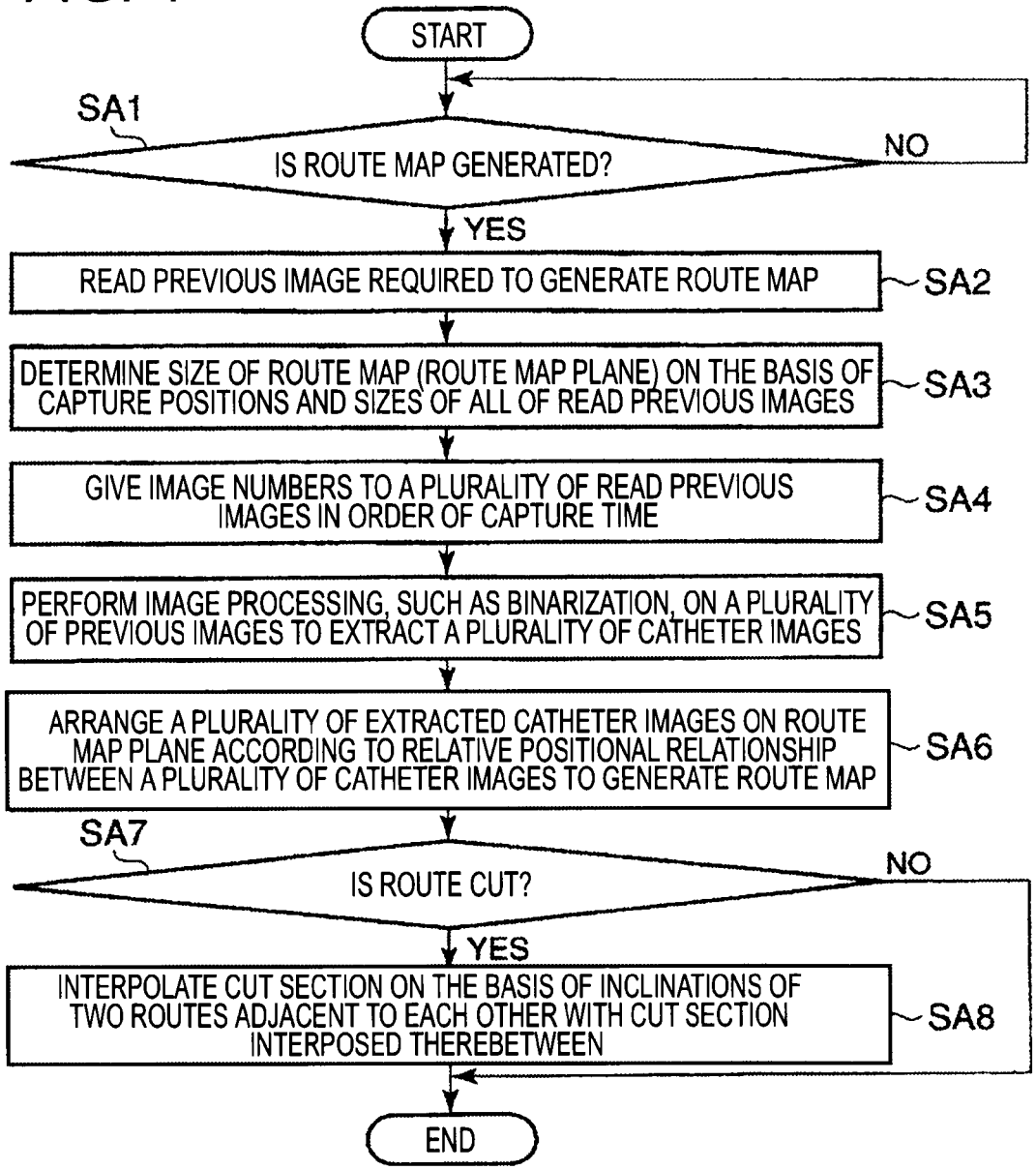

ROUTE MAP

| PATIENT ID | EXAMINATION ID | ROUTE MAP ID |
|---|---|---|
| 00000001 | 100 | 001 |
| 00000002 | 101 | 002 |
| 00000003 | 102 | 003 |

IMAGE DISPLAY APPARATUS AND IMAGE DISPLAY SYSTEM

CROSS-REFERENCE TO RELATED APPLICATIONS

This application is based upon and claims the benefit of priority from prior Japanese Patent Application No. 2008-021492, filed Jan. 31, 2008, the entire contents of which are incorporated herein by reference.

BACKGROUND OF THE INVENTION

1. Field of the Invention

The present invention relates to an image display apparatus and an image display system for supporting a catheter operation.

2. Description of the Related Art

An IVR (Interventional Radiology) procedure using an image generating apparatus, such as an X-ray diagnostic apparatus, to treat a site of lesion has been actively performed. In the IVR procedure, a catheter operation is performed for angioplasty or angioembolization. In recent years, various techniques have been proposed which support an operation of inserting a medical instrument, such as a catheter, into a site of lesion during the IVR procedure (for example, see JP-A-2000-342565). A system for performing the IVR procedure includes the above-mentioned image generating apparatus, an image management apparatus (PACS: Picture Archiving and Communication System), and an image observation apparatus. The image management apparatus stores images obtained during the procedure. The image observation apparatus is for observing the images. The image observation apparatus is installed in an examination room where the procedure is performed.

During the procedure, in some cases, the physician wants to refer to the images obtained during the previous procedure. In order to refer to the images obtained during the previous procedure, it is necessary to manually input identification information of each image to the image observation apparatus. However, during the procedure, the movement of the physician's hands is restricted since the physician operates the catheter. Therefore, the images to be referred need to be set in advance. In some cases, the technician inputs the identification information of each image according to instructions from the physician. However, in this case, it takes a long time to search an image suitable for the procedure. At that time, the procedure is temporarily discontinued. As a result, the efficiency of the procedure is lowered or patient's costs are increased.

BRIEF SUMMARY OF THE INVENTION

An object of the invention is to provide an image display apparatus and an image display system capable of improving the efficiency of an IVR procedure.

According to a first aspect of the invention, an image display apparatus includes: a storage unit that stores data of a plurality of previous images of different regions associated with a plurality of positions generated during a previous catheter procedure; a specifying unit that specifies a specific portion of a catheter image from a current image generated during a current catheter procedure; and a display unit that displays a specific previous image corresponding to the position of the specified specific portion among the plurality of previous images.

According to a second aspect of the invention, an image display apparatus includes: a storage unit that stores data of a plurality of previous images of a plurality of regions generated during a previous catheter procedure; a generating unit that arranges a plurality of first catheter images or blood vessel images included in each of the plurality of previous images according to the positional relationship between the plurality of regions to generate a route map indicating the distribution of the plurality of first catheter images or blood vessel images; a first specifying unit that specifies a specific portion of a second catheter image included in a current image generated during a current catheter procedure; a first calculating unit that calculates the position of the specified specific portion on the route map on the basis of the positional relationship between the current image and the previous image; and a display unit that displays a specific previous image corresponding to the calculated position among the plurality of previous images.

According to a third aspect of the invention, an image display system includes: an image generating apparatus; an image management apparatus; and an image observation apparatus. The image generating apparatus includes: a generating unit that generates data of a current image during a current catheter procedure; and a first transmitting unit that transmits the generated data of the current image to the image management apparatus. The image management apparatus includes: a storage unit that stores data of a plurality of previous images of different regions associated with a plurality of positions generated during a previous catheter procedure; a specifying unit that specifies a catheter image from the received current image; a selecting unit that selects data of a specific previous image corresponding to the position of the specified catheter image from the data of the plurality of previous images; and a second transmitting unit that transmits the selected data of the specific previous image to the image observation apparatus. The image observation apparatus includes a display unit that displays the received specific previous image.

According to a fourth aspect of the invention, an image display system includes: an image generating apparatus; a camera apparatus; an image management apparatus; and an image observation apparatus. The image generating apparatus includes: a generating unit that generates data of a current image during a current catheter procedure; and a first display unit that displays the generated current image. The camera apparatus captures the image of the displayed current image to generate video data and transmits the generated video data to the image management apparatus. The image management apparatus includes: a storage unit that stores data of a plurality of previous images of different regions associated with a plurality of positions generated during a previous catheter procedure; a specifying unit that specifies a catheter image from the received video data; a selecting unit that selects data of a specific previous image corresponding to the position of the specified catheter image from the data of the plurality of previous images; and a second transmitting unit that transmits the selected data of the specific previous image to the image observation apparatus. The image observation apparatus includes a second display unit that displays the received specific previous image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a diagram illustrating the outline of the operation of the image display system shown in FIG. 1.

FIG. 4 is a flowchart illustrating a route map generating process performed by a route map generating unit shown in FIG. 3.

FIG. 5 is a diagram illustrating a table indicating correspondence between image numbers and previous images stored in a storage unit shown in FIG. 3.

DETAILED DESCRIPTION OF THE INVENTION

Hereinafter, an image display apparatus and an image display system according to embodiments of the invention will be described with reference to the accompanying drawings.

The image display system according to this embodiment is a navigation system for enabling a physician to insert a medical instrument (for example, a catheter or a guide wire) into a site of lesion during an IVR procedure. In general, the IVR procedure is not performed on the same examinee once, but is performed for a predetermined period of time (for example, for one month or a half year) several times. In addition, images generated during the IVR procedure are stored.

This embodiment automatically selects an image corresponding to the position of a catheter during the current IVR procedure from a plurality of images obtained during the previous IVR procedure and displays the selected image during the current IVR procedure.

Figure 1:
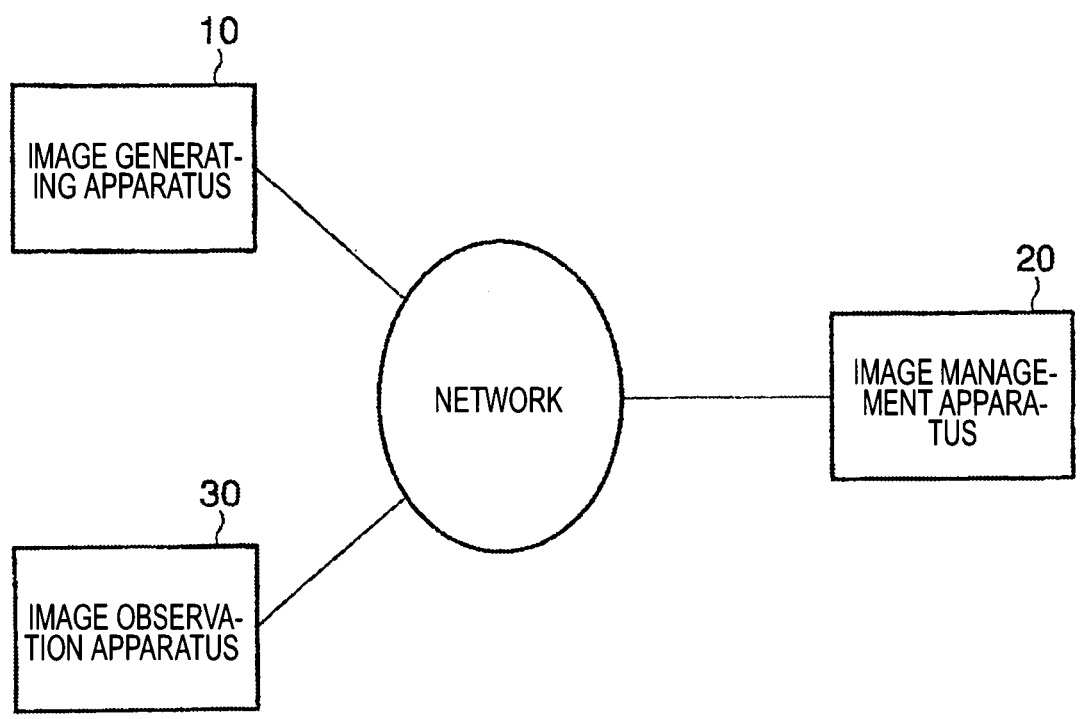
FIG. 1 is a diagram illustrating the structure of an image display system according to an embodiment of the invention.

FIG. 1 is a diagram illustrating the structure of the image display system according to this embodiment. As shown in FIG. 1, the image display system includes an image generating apparatus (X-ray diagnostic apparatus) 10, an image management apparatus (PACS) 20, and an image observation apparatus (computer) 30 that are connected to one another through a network.

The image generating apparatus 10 performs radiography or radioscopy on an examinee during the IVR procedure to generate image data such as a radiographic image or a radioscopic image. The image data is associated with the capture position thereof. The capture position is, for example, the position of an X-ray detector of the image generating apparatus 10 during radiography or radioscopy. During the IVR procedure, for example, the image generating apparatus 10 generates a plurality of image data for a plurality of parts from a catheter inserting portion to a site of lesion (for example, a lung blood vessel). Each image includes a catheter image.

Hereinafter, a set of a plurality of images generated by one IVR procedure is referred to as a procedure image set. In addition, an image generated by the current IVR procedure is referred to as a current image, and an image generated by the previous IVR procedure is referred to as a previous image.

The image management apparatus 20 manages a plurality of image data of a plurality of procedure image sets generated by the image generating apparatus 10 in a format based on, for example, a DICOM (Digital Imaging and Communication in Medicine) standard. The image management apparatus 20 generates one route map on the basis of a plurality of previous images included in one procedure image set. The route map is generated by arranging a plurality of catheter images included in a plurality of previous images according to the relative positional relationship between the plurality of catheter images. The route map indicates the distribution of a plurality of catheter images, that is, a route through which the catheter passes during the previous IVR procedure. During the current IVR procedure, the image management apparatus 20 receives data of the current image, specifies the current position of the leading end of the catheter from the current image using the route map, automatically selects a previous image corresponding to the specified current position of the leading end of the catheter from a plurality of previous images, and transmits the selected previous image to the image observation apparatus 30. This automatic selection and transmission function will be described in detail below.

The image observation apparatus 30 is installed in an examination room where the procedure is performed. The image observation apparatus 30 displays, for example, the current image, the previous image, and the route map received from the image generating apparatus 10 or the image management apparatus 20.

As described above, the image generating apparatus 10, the image management apparatus 20, and the image observation apparatus 30 are individual apparatuses connected to one another through a network. However, this embodiment is not limited thereto. For example, the image generating apparatus, the image management apparatus, and the image observation apparatus are integrated into one apparatus (image display apparatus).

(Catheter Operating Process)

First, during the IVR procedure, a catheter operating process will be described.

Process 1 (DSA): It is necessary to use the image display device 10 to generate data for the image of a blood vessel in order to check the shape of the blood vessel before a catheter is inserted. The image of the blood vessel is generated as follows: 1. Before a catheter is inserted, the image generating apparatus 10 performs radiography to generate data of a mask image; 2. The physician injects a contrast agent from the leading end of the catheter; 3. The image generating apparatus 10 generates data of a contrast image; and 4. The image generating apparatus 10 subtracts the mask image from the contrast image to generate data of a blood vessel image for checking the shape of the blood vessel.

Process 2 (the movement of the catheter): When the data of the blood vessel image is generated, the image generating apparatus 10 performs radioscopy on an examinee to generate data of a radioscopic image (current image) in real time. The physician inserts the catheter into a site of lesion while referring to the blood vessel image and the radioscopic image. When the physician wants to obtain a detailed image while the catheter is moved, radiography may be performed to generate a radiographic image.

Process 3: When the catheter is moved to a position where the physician wants to check the shape of the blood vessel, the physician temporarily discontinues the radioscopic operation of the image generating apparatus 10. Then, the physician performs Process 1 (DSA) again to generate data of a new blood vessel image. Then, the physician performs Process 2 (the movement of the catheter). The physician repeatedly performs these processes to move the catheter to the site of lesion.

(Outline of Process of Image Display System)

FIG. 2 is a diagram illustrating the outline of a route map generating process and a process of automatically selecting and displaying the previous image performed by the image display system according to this embodiment during the current IVR procedure.

First, before the current IVR procedure is performed, a route map is generated in advance. For simplicity of description, it is assumed that the previous images forming the route map include a first previous image PI1, a second previous image PI2, and a third previous image PI3. The first previous image includes a catheter insertion portion SP. The third previous image includes a site of lesion GP. These previous images are radiographic images related to different parts of the examinee, that is, radiographic regions. These previous images each include a catheter image. These previous images may be radioscopic images or radiographic images, such as mask images. The image management apparatus 20 arranges these previous images PI1, PI2, and PI3 on a route map plane RP according to the capture positions, thereby generating a route map RM. That is, the image management apparatus 20 combines three catheter images included in the previous images PI1, PI2, and PI3 to generate the route map RM. As such, the route map shows a plurality of catheter images laid across a plurality of capture regions on one plane.

During the current IVR procedure, the image generating apparatus 10 generates the current image CI of an examinee P, and transmits the generated current image CI to the image management apparatus 20. The current image CI may be a radioscopic image or a radiographic image, such as a mask image. The image management apparatus 20 calculates the position of a specific portion (typically, the leading end of a catheter) of the catheter image included in the current image CI on the route map RM, selects the previous image (for example, the second previous image PI2) next to the current position CP of the leading end of the catheter from a plurality of previous images, and transmits the selected previous image to the image observation apparatus 30. The image observation apparatus 30 displays the received previous image.

(Structure of Image Management Apparatus 20)

Figure 3:
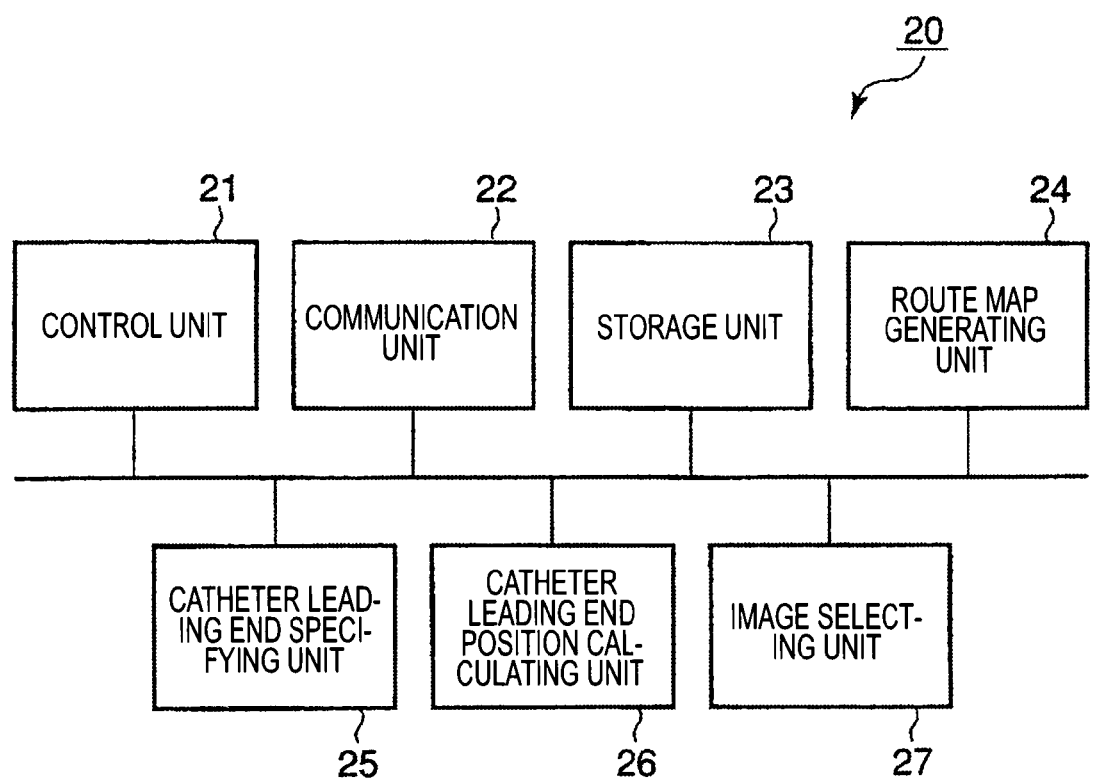
FIG. 3 is a diagram illustrating the structure of an image management apparatus shown in FIG. 1.

FIG. 3 is a diagram illustrating the structure of the image management apparatus 20. As shown in FIG. 3, the image management apparatus 20 includes a control unit 21, a communication unit 22, a storage unit 23, a route map generating unit 24, a catheter leading end specifying unit 25, a catheter leading end position calculating unit 26, and an image selecting unit 27.

The communication unit 21 receives various data, such as image data, from the image generating apparatus 10 or the image observation apparatus 30, or transmits various data to the image generating apparatus 10 or the image observation apparatus 30.

The storage unit 23 stores procedure identification information, such as an examination ID, so as to be associated with the procedure image set. The storage unit 23 stores image identification information (for example, an image ID) or a capture position so as to be associated with the previous image included in the procedure image set. In addition, the storage unit 23 stores procedure identification information so as to be associated with the route map generated by the route map generating unit 24, which will be described below. Further, the storage unit 23 stores image identification information or a capture position so as to be associated with the current image.

The route map generating unit 24 performs a route map generating process to generate one route map on the basis of a plurality of previous images included in one procedure image set. Specifically, the route map generating unit 24 generates a route map by arranging a plurality of catheter images included in a plurality of previous images according to the relative positional relationship between the regions where a plurality of previous images are captured (the relative positional relationship between the positions where the previous images are captured). That is, the route map generating unit 24 arranges a plurality of catheter images on a route map plane according to the relative positional relationship between a plurality of catheter images to generate a route map. The route map plane is a space in a memory where a plurality of previous images are arranged. The route map plane is represented by a patient coordinate system having the long axis of the bed on which the examinee is laid as the Z-axis and the short axis of the bed as the X-axis. The route map may use all the previous images included in a corresponding procedure image set, or it may use a plurality of previous images appropriately selected from all the previous images (for example, at a predetermined time interval or a predetermined gap between the positions). Pixels of each route portion forming the route of the route map are allocated with image identification information of a previous image corresponding to each route portion. The route map generating process will be described in detail below.

The catheter leading end specifying unit 25 specifies the image of the leading end of the catheter included in the current image on the basis of the shape of the leading end of the catheter.

The catheter leading end position calculating unit 26 calculates the position of the leading end of the catheter on the route map on the basis of the capture position of the current image and the position of the leading end of the catheter on the current image.

The image selecting unit 27 selects a previous image corresponding to the calculated position of the leading end of the catheter on the route map from a plurality of previous images stored in the storage unit 23. For example, the image selecting unit 27 specifies image identification information allocated to the pixel located at a position that is spaced a predetermined distance from the current position of the leading end of the catheter to a site of lesion on the route, searches the storage unit 23 using the specified image identification information as a key, and specifies the corresponding previous image. The selected previous image is transmitted to the image observation apparatus 30 through the communication unit 22.

(Route Map Generating Process)

Next, the route map generating process will be described in detail. FIG. 4 is a flowchart illustrating the route map generating process. The control unit 21 waits for a route map generating request (Step SA1). When the physician inputs a request to start the route map generating process to the image management apparatus 20 through the image observation apparatus 30 (Step SA1: YES), the control unit 21 controls the route map generating unit 24 to perform the route map generating process. The physician inputs the procedure identification information of a procedure image set, which is the root of the currently generated route map, through the image observation apparatus 30 to request the start of the route map generating process. Specifically, the procedure identification information is at least one of a patient ID, an examination ID, an examination date, and a Study/Series UID.

First, the route map generating unit 24 selects the previous image required to generate the route map and reads the selected previous image (Step SA2). For example, the route map generating unit 24 searches a corresponding procedure image set from the storage unit 23 using the procedure identification information as a key, and reads a plurality of previous images included in the specified procedure image set.

The route map generating unit 24 determines the coordinates and the size of a route map plane on the basis of the capture positions and the sizes of all of the read previous images (Step SA3). The route map generating unit 24 allocates image identification information, such as image numbers, to the read previous images, according to the capture time of the previous images (Step SA4).

FIG. 5 is a diagram illustrating an example of a table indicating correspondence between the image numbers and the previous images (hereinafter, referred to as an image number correspondence table). As shown in FIG. 5, the image number correspondence table includes a route map ID field for identifying a route map, an image number field, and a previous image file name field. For example, image number 1 is given to a previous image having a file name 'Image05.dcm'. The image number correspondence table is stored in the storage unit 23.

The route map generating unit 24 performs image processing, such as binarization, on a plurality of previous images to extract a plurality of catheter images (Step SA5). For example, a pixel value of "1" is allocated to the pixels of the catheter image, and a pixel value of "0" is allocated to pixels other than the pixels of the catheter image. The route map generating unit 24 arranges the extracted catheter images on the route map plane according to the relative positional relationship (the capture positions of the previous images) between a plurality of catheter images, thereby generating a route map (Step SA6).

Specifically, first, the route map generating unit 24 calculates the position of each of the pixels forming the catheter image on the route map (patient coordinate system), on the basis of the capture position of the previous image related to the catheter image and the positions of the pixels of the previous image. The position of the pixel of the previous image is defined by, for example, the distance from the base point (for example, the end point or the central point) of the previous image to the pixel. Then, the route map generating unit 24 allocates an image number to the pixel disposed at the calculated position on the route map. In this way, the catheter image is arranged on the route map. The catheter image arranged on the route map is referred to as a route portion. A route portion related to an n-th image and a route portion related to an (n−1)-th image may at least partially overlap each other. In this case, any of the image numbers of the overlap portion (for example, the (n−1)-th image having a small image number) is used.

When all the catheter images are arranged on the route map plane, the route map generating unit 24 performs image processing, such as segmentation, to determine whether the route is cut (Step SA7). If it is determined that the route is cut (Step SA7: YES), the route map generating unit 24 interpolates the cut section on the basis of the inclinations of two route portions adjacent to each other with the cut section interposed therebetween on the route map (Step SA8). The route interpolation process will be described in detail below.

If it is determined that the route is not cut (Step SA7: NO), a route map is completed, and the route map generating process ends.

Figure 6:
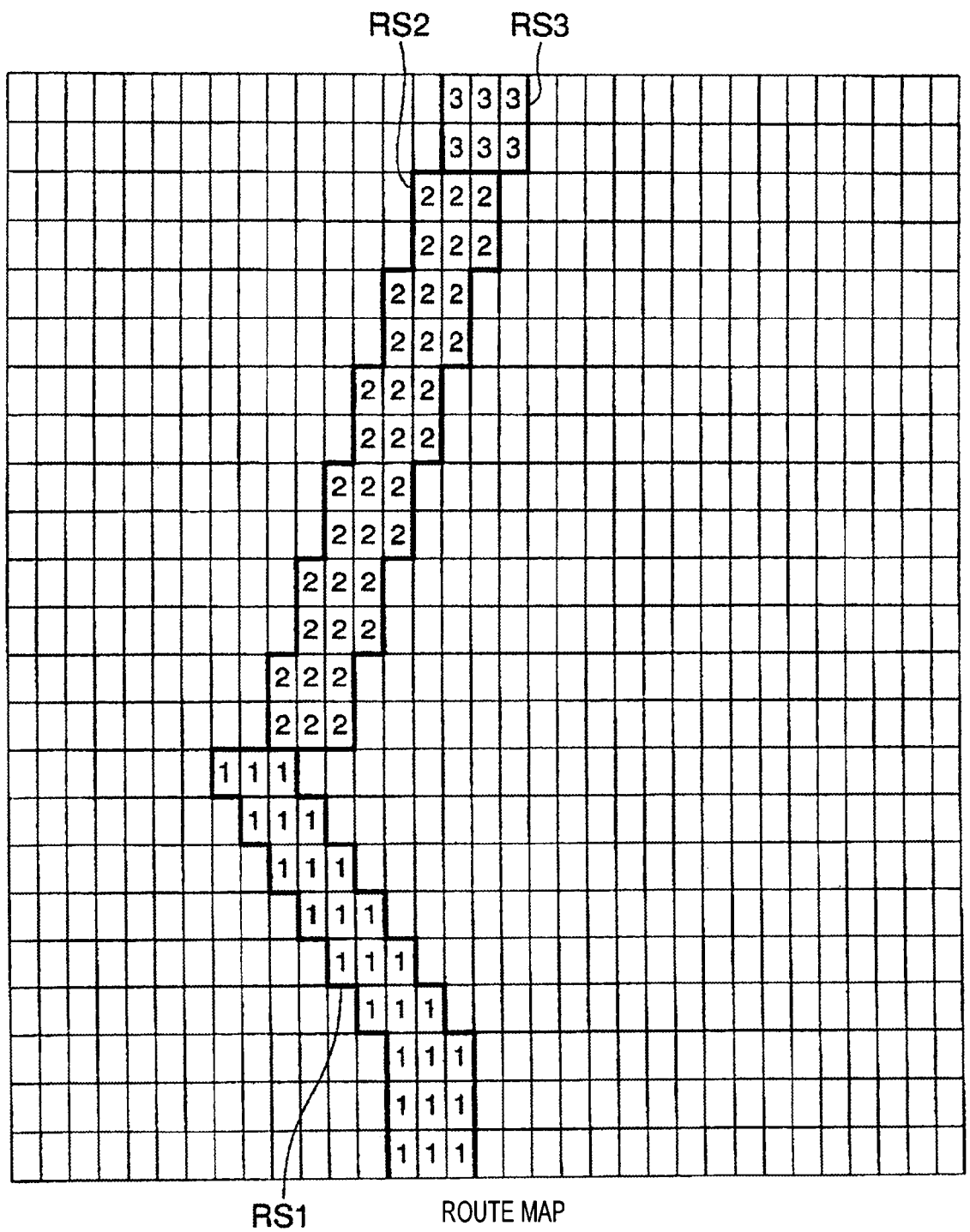
FIG. 6 is a diagram illustrating an example of a route map generated by a route map generating unit shown in FIG. 3.

If it is determined in Step SA7 that the route is not cut (Step SA7: NO), or when the cut section is interpolated (Step SA8), a route map is completed, and the route map generating unit 24 ends the route map generating process. FIG. 6 is a diagram illustrating an example of the route map. As shown in FIG. 6, the route map shows the route of the catheter during the previous IVR procedure derived from the route map. The number of the previous image is given to the pixels forming the route. For example, a first route portion RS1 is derived from the catheter image included in the previous image having image number '1'.

Figures 7, 8:
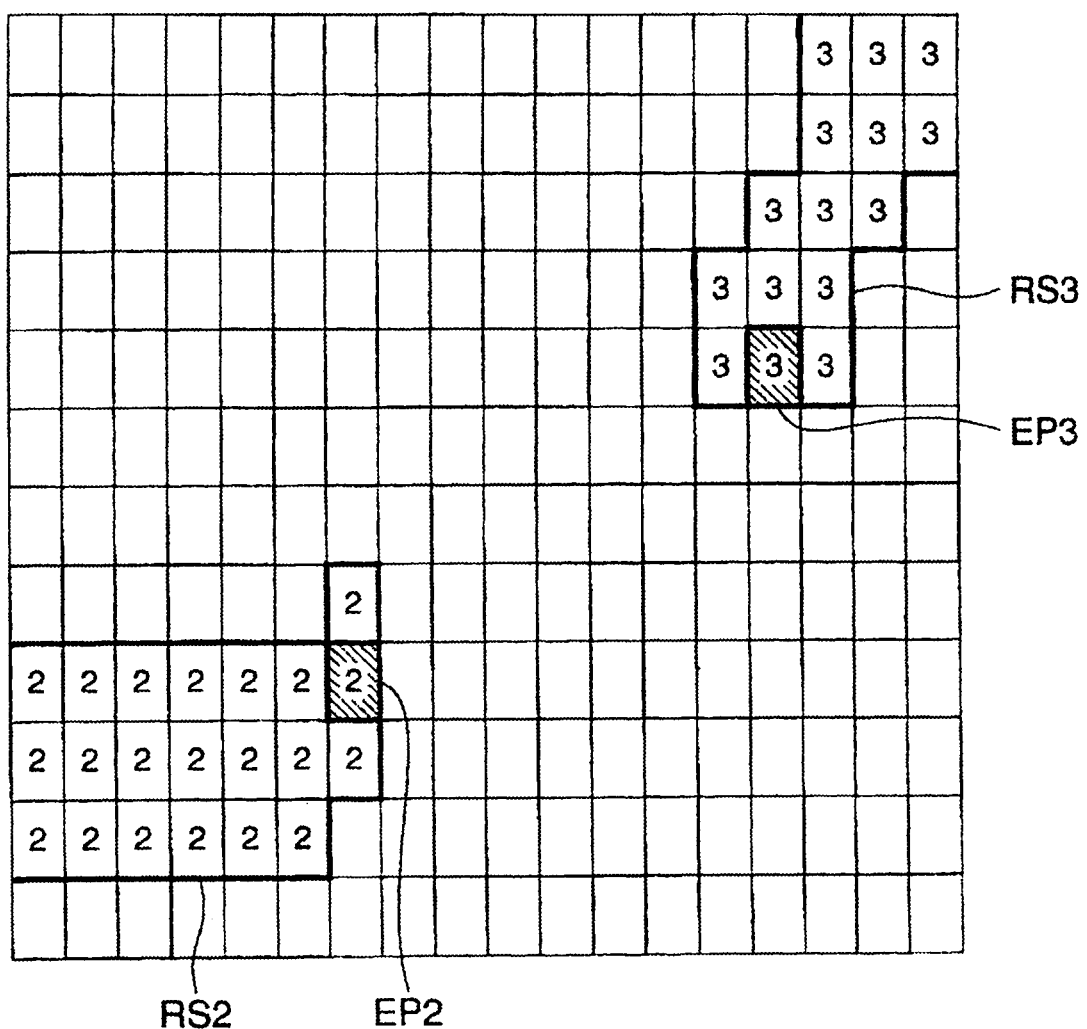
FIG. 7 is a diagram illustrating a table indicating correspondence between a route map and examination identification information stored in the storage unit shown in FIG. 3.
FIG. 8 is a diagram illustrating Step SA8 (route interpolation process) shown in FIG. 4.

The storage unit 23 stores the generated route map so as to be associated with examination identification information, such as a patient ID or an examination ID. FIG. 7 is a diagram illustrating an example of a table indicating the correspondence between a route map and examination identification information (hereinafter, referred to as a route map correspondence table). As shown in FIG. 7, the route map correspondence table includes a patient ID field, an IVR procedure examination ID field, and a route map ID field. For example, a route map ID '001' is associated with a patient ID '00000001' and an examination ID '100'.

Next, Step SA8 (route interpolation process) in the route map generating process performed by the route map generating unit 24 will be described in detail. FIG. 8 is a diagram illustrating a route map having a cut portion. As shown in FIG. 8, there is a cut portion between a route portion RS2 that is given image number '2' and a route portion RS3 that is given image number '3'. As shown in FIG. 8, first, the route map generating unit 24 specifies end points EP2 and EP3 of the route portions. Specifically, first, the route map generating unit 24 makes the route portions RS2 and RS3 thin. In FIG. 8, the pixels forming the thin lines (hereinafter, referred to as thin line pixels) are represented by bold image numbers.

Then, the route map generating unit 24 sets a thin line pixel having only one adjacent thin line pixel as an end point EP.

Figure 9:
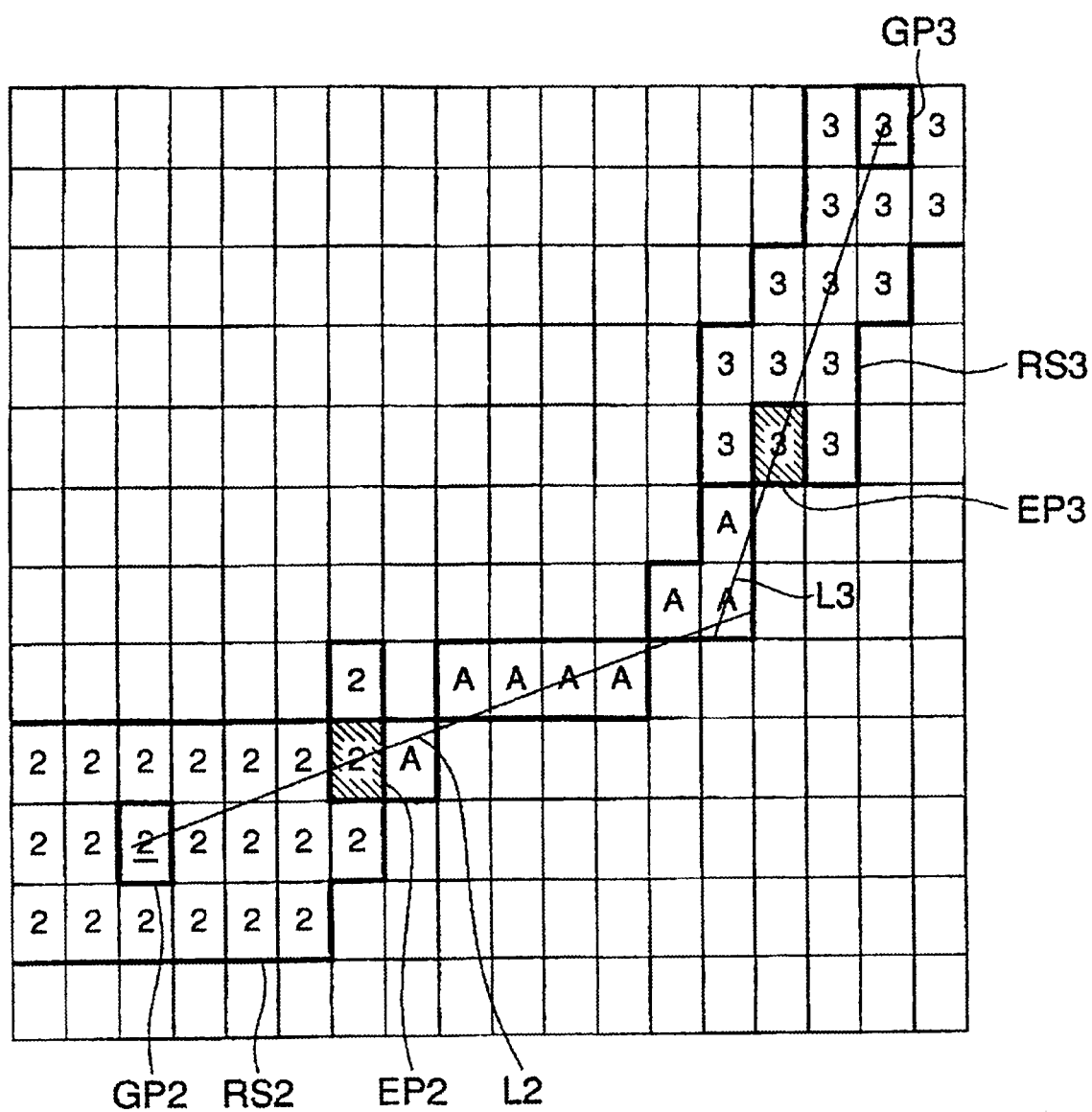
FIG. 9 is another diagram illustrating Step SA8 (route interpolation process) shown in FIG. 4.

Then, as shown in FIG. 9, in order to obtain the inclinations of the route portions RS2 and RS3, the route map generating unit 24 sets thin line pixels GP2 and GP3 (hereinafter, referred to as guide points) that are spaced a predetermined distance (for example, four pixels) from the end point EP in the route portions RS2 and RS3. In FIG. 9, the guide point is a pixel having an underlined image number. Then, the route map generating unit 24 sets straight lines L2 and L3 (inclination) respectively drawn from the guide points GP2 and GP3 to the end points EP2 and EP3 in the route portions RS2 and RS3. The two straight lines L2 and L3 extend through the pixels until they intersect each other. The pixels on the extension line (hereinafter, referred to as interpolation pixels) are given image number 'A' indicating that the pixel has been interpolated. In this way, the route portion RS2 and the route portion RS3 are connected to each other by an extension line composed of a plurality of interpolation pixels.

Figure 10:
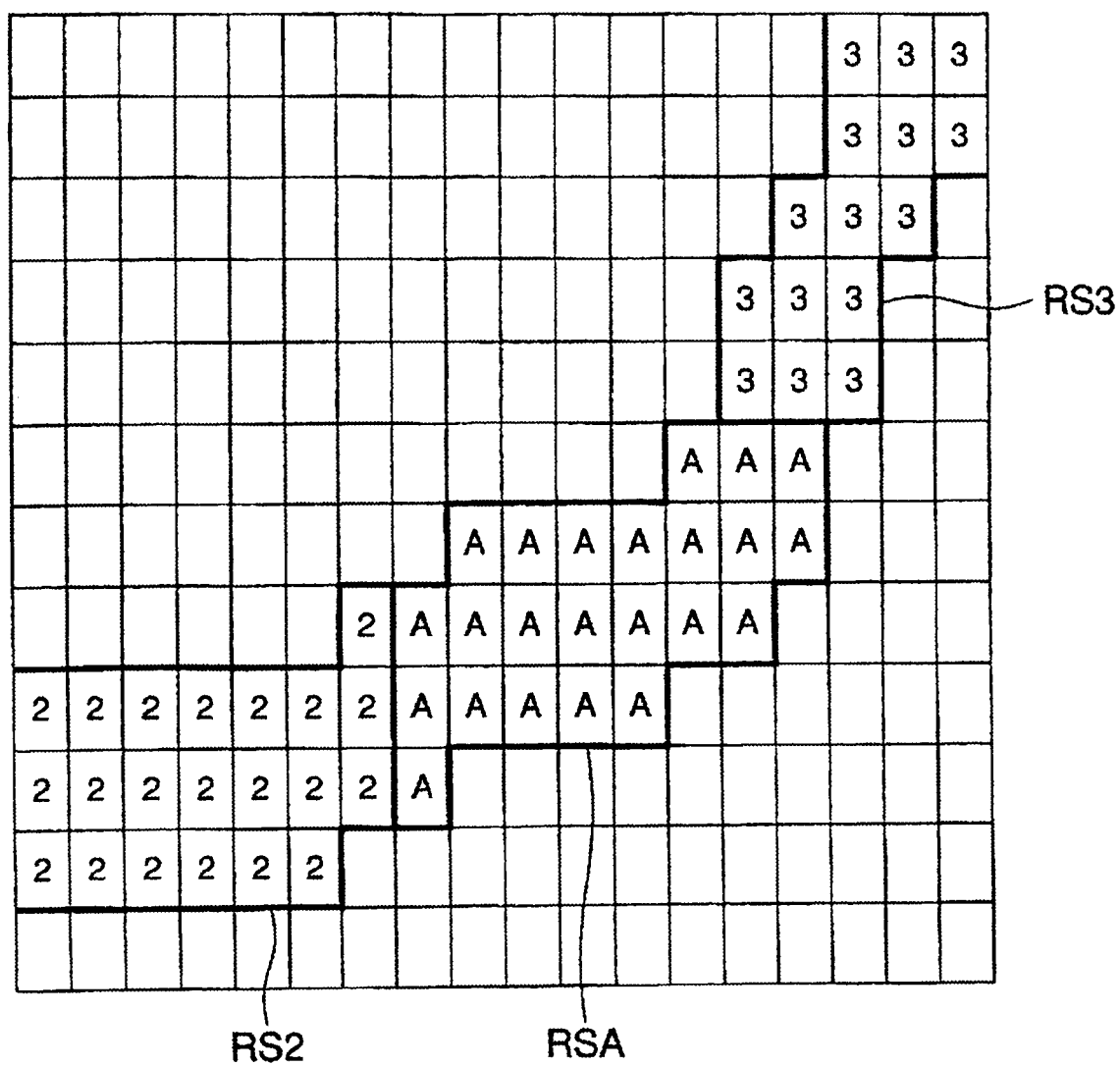
FIG. 10 is still another diagram illustrating Step SA8 (route interpolation process) shown in FIG. 4.

As shown in FIG. 10, the route map generating unit 24 extends the extension line composed of the interpolation pixels to be substantially equal to the width of the adjacent route portions RS2 and RS3 to interpolate the cut portion. Specifically, among the pixels that are not given image numbers, pixels adjacent to the extension line in the vertical direction or the horizontal direction are given the image number 'A'. As a result, the extension line is extended to form a route portion RSA.

As described above, in Step SA7, the route map generating unit 24 interpolates the cut portion to the route portion RSA on the basis of the inclination of the route portion RS2 and the inclination of the route portion RS3. Then, the interpolation process in Step SA9 ends. The image number 'A' of the interpolated portion may be substituted for the image number (image number 2 or image number 3) of a route adjacent to the interpolated portion. In the above-mentioned interpolation method, the cut portion between the route portion RS2 and the route portion RS3 is interpolated by a straight line. However, the cut portion may be interpolated by a high-dimensional line, such as a two-dimensional curved line or a three-dimensional curved line. In addition, the route map generating unit 24 may correct the interpolated route portion RSA in response to instructions input through the image observation apparatus 30 from the physician.

(Automatic Selection and Display Process of Previous Image)

Next, a clinical application of a process of automatically selecting and displaying the previous image using the route map during the current IVR procedure will be described. In some cases, the physician wants to check the content of the previous IVR procedure during the current IVR procedure. For example, the physician wants to check the route of the catheter obtained by the previous IVR procedure, whether there is an embolus in the blood vessel into which the catheter is inserted, the state of a stent put into the blood vessel, and the content of the previous operation.

Figure 11:
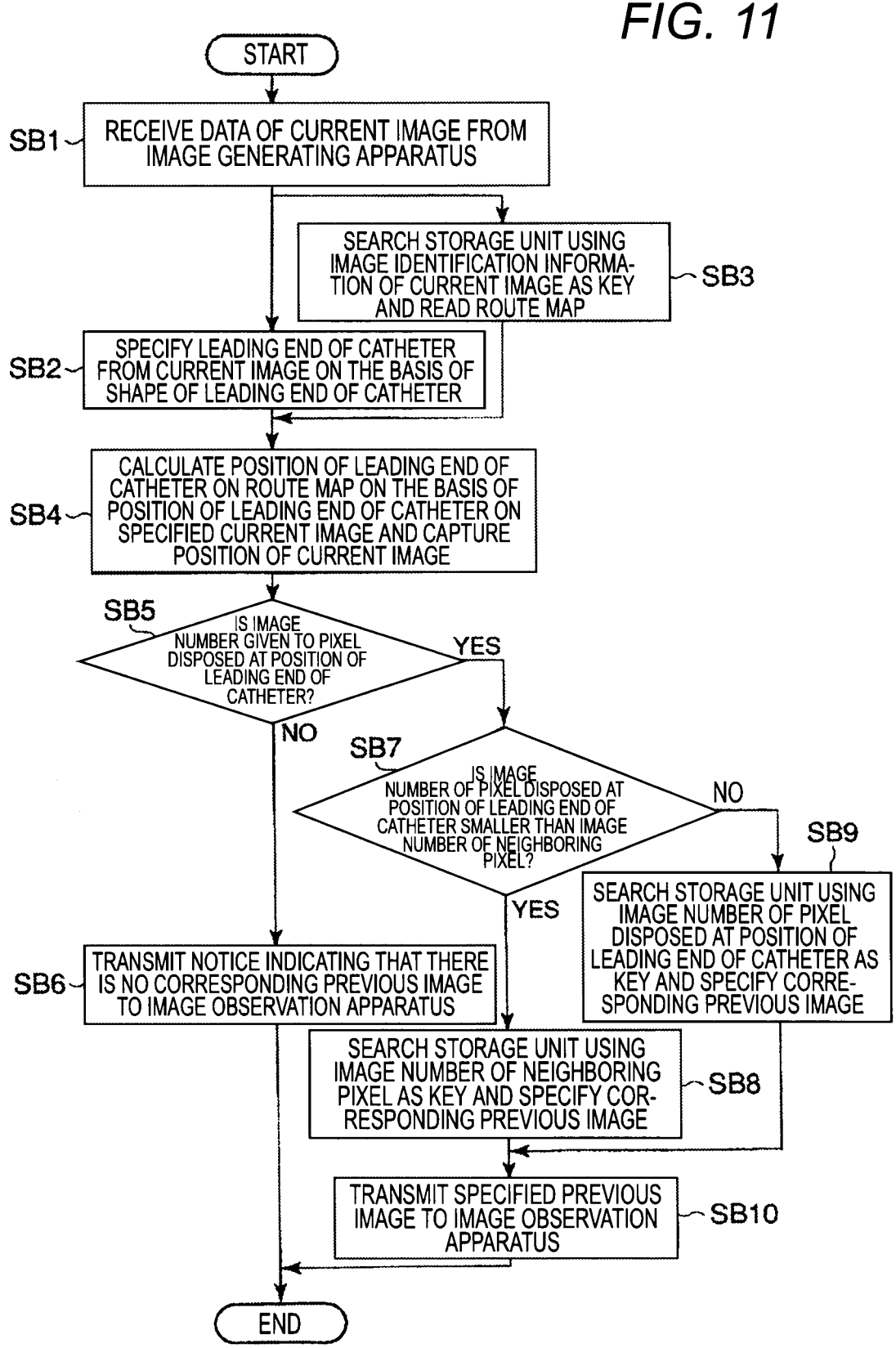
FIG. 11 is a flowchart illustrating a process of automatically searching and transmitting the previous image performed by a control unit 21 shown in FIG. 3.

FIG. 11 is a flowchart illustrating a process of automatically searching and transmitting the previous image performed by the control unit 21 of the image management apparatus 20. First, the control unit 21 receives data of the current image transmitted from the image generating apparatus 10 through the communication unit 22 (Step SB1). The current image may be a radioscopic image or a contrast image. For example, image identification information, such as a patient ID of an examinee, or the capture position of the current image is attached to the received current image. The received current image is stored in the storage unit 23 so as to be associated with the image identification information and the capture position.

When receiving the current image, the control unit 21 controls the catheter leading end specifying unit 25 to perform a catheter leading end specifying process, and controls the image selecting unit 27 to read a route map.

In the catheter leading end specifying process, the catheter leading end specifying unit 25 specifies the image of the leading end of the catheter included in the current image on the basis of the shape of the leading end of the catheter (Step SB2). In the route map reading process, the image selecting unit 27 searches the storage unit 23 using the patient ID attached to the current image as a key, specifies a route map having the patient ID, and reads the specified route map (Step SB3).

When Step SB2 and Step SB3 end, the control unit 21 controls the catheter leading end position calculating unit 26 to calculate the position of the leading end of the catheter. In the process of calculating the leading end of the catheter, the catheter leading end position calculating unit 26 calculates the position of the leading end of the catheter on the route map, on the basis of the capture position of the current image and the position of the leading end of the catheter on the current image (Step SB4). Specifically, the catheter leading end position calculating unit 26 calculates the current position of the leading end of the catheter on the route map (patient coordinate system), on the basis of the capture position of the current image and the distance from the base point (for example, the end point or the central point) of the current image to the position of the leading end of the catheter in the coordinate system of the current image. When there is a mismatch between the capture position of the previous image and the capture position of the current image, a value for correcting the mismatch is obtained by calculating the positional deviation of the same point of the examinee in anatomy (for example, a bone, such as the femur, disposed at the same position) on the image. Then, the current position of the leading end of the catheter on the route map is calculated on the basis of the capture position of the current image, the distance from the base point to the position of the leading end of the catheter on the current image, and the correction value.

When the position of the leading end of the catheter on the route map is calculated, the control unit 21 controls the image selecting unit 27 to determine whether an image number is given. In the process of determining whether the image number is given, the image selecting unit 27 determines whether an image number is given to the pixel disposed at the position of the leading end of the catheter on the route map (Step SB5).

If it is determined that no image number is given (Step SB5: NO), the control unit 21 transmits a notice indicating that there is no corresponding previous image to the image observation apparatus 30 through the communication unit 22 (Step SB6). The transmitted notice is displayed on the image observation apparatus 30.

If it is determined that an image number is given (Step SB5: YES), the control unit 21 controls the image selecting unit 27 to perform an image number comparing process. In the image number comparing process, the image number selecting unit 27 searches the pixels in the vicinity of the position of the leading end of the catheter, and determines whether the image number of the neighboring pixel is larger than the image number of the pixel disposed at the position of the leading end of the catheter (Step SB7). The neighboring pixel means a pixel that is spaced a predetermined distance (for example, five pixels) from the position of the leading end of the catheter to a site of lesion on the route. The physician can use the image observation apparatus 30 to arbitrarily set the predetermined distance.

If it is determined that the image number of the neighboring pixel is larger than the image number of the pixel disposed at the position of the leading end of the catheter (Step SB7: YES), the control unit 21 controls the image selecting unit 27 to perform a first previous image selecting process. In the first previous image selecting process, the image selecting unit 27 searches the storage unit 23 using the image number of the neighboring pixel as a key, and specifies a previous image having the corresponding image number from a plurality of previous images (Step SB8).

If it is determined that the image number of the neighboring pixel is not larger than the image number of the pixel disposed at the position of the leading end of the catheter, that is, the image numbers are equal to each other (Step SB7: NO), the control unit 21 controls the image selecting unit 27 to perform a second previous image selecting process. In the second previous image selecting process, the image selecting unit 27 searches the storage unit 23 using the image number of the pixel disposed at the position of the leading end of the catheter as a key, and specifies a previous image having the corresponding image number from a plurality of previous images (Step SB9).

When Step SB8 or Step SB9 ends, the control unit 21 transmits the specified previous image to the image observation apparatus 30 through the communication unit 22 (Step SB10). The received previous image is displayed on the image observation apparatus 30. The image observation apparatus 30 may display the route map and the previous image or the current image at the same time. When there is an interpolated portion in the route map, the interpolated portion may be displayed separately from the route portion. In addition, the image observation apparatus 30 may display the route map such that the position of the leading end of the catheter is clearly specified on the route map. Further, the image observation apparatus 30 may display the route map such that the position of the previous image is clearly specified on the route map. Furthermore, the image observation apparatus 30 may display the route map such that other portions, such as a target point during the previous IVR procedure (for example, the site of lesion GP in FIG. 2), are clearly specified on the route map. As the clearly specifying method, any of the following methods may be used: a method of displaying the pixel of the specified portion in a color that is different from those of the other pixels: a method of blinking the pixel of the specified portion; and a method of displaying the pixel of the specified portion with different brightness. In addition, a mark may be attached to the specified portion.

The processes from Steps SB7 to SB10 are performed on the basis of the following concept. The previous image is displayed in order to check the shape of a blood vessel into which the catheter is inserted in advance. Therefore, the previous image that the physician wants to display is an image of the forward location of the current position of the leading end of the catheter, and there is no point in displaying an image being far away from the current position of the leading end of the catheter.

Figure 12:
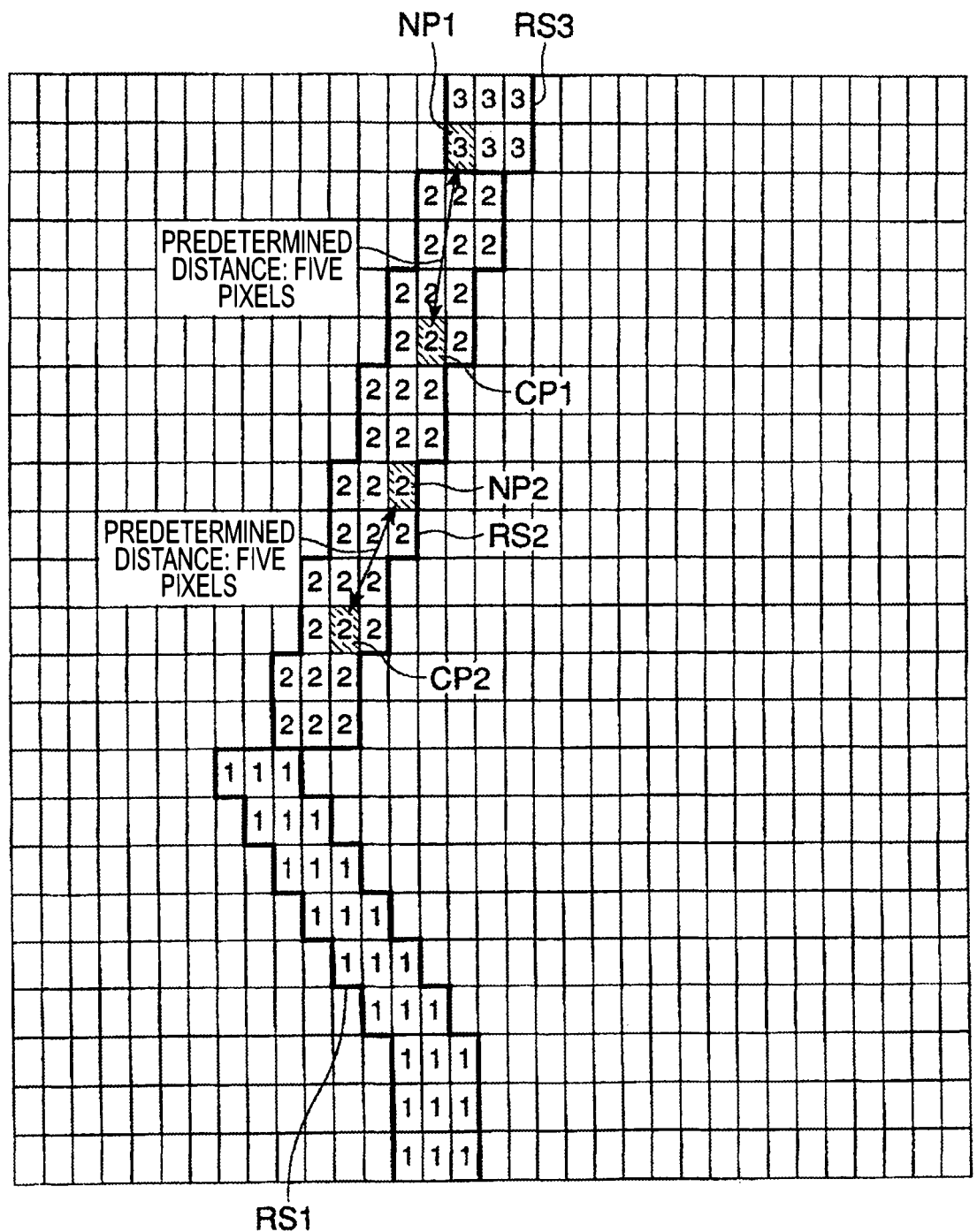
FIG. 12 is a diagram illustrating in detail processes from Step SB7 to Step SB10 shown in FIG. 11.

FIG. 12 is a diagram illustrating the processes from Step SB7 to Step SB10 in detail. As shown in FIG. 12, the following pixels are considered: a first pixel CP1 disposed at the position of the leading end of the catheter; a neighboring pixel NP1 corresponding to the pixel CP1; a second pixel CP2 disposed at the position of the leading end of the catheter; and a neighboring pixel NP2 corresponding to the pixel CP2. In addition, the neighboring pixel is set at a position that is spaced five pixels from the position of the leading end of the catheter.

As shown in FIG. 12, the first pixel CP1 is disposed on a route portion RS2. The neighboring pixel NP1 of the first pixel CP1 is disposed on a route portion RS3. In this case, since the image number '3' of the neighboring pixel NP1 is larger than the image number '2' of the pixel CP1, the previous image having the image number '3' is selected in Step SB8. That is, the previous image related to the position that is slightly ahead of the current position of the leading end of the catheter is displayed. In addition, as shown in FIG. 12, the second pixel CP2 is disposed on the route portion RS2, and is spaced six or more pixels from the route portion RS3. Therefore, the neighboring pixel NP2 corresponding to the pixel CP2 is also disposed on the route portion RS2. In this case, since the image number '2' of the pixel CP1 is equal to the image number '2' of the neighboring pixel NP1, the previous image having the image number '2' is selected in Step SB9. Therefore, according to the above-mentioned automatic selection and display process, the previous image related to an appropriate position corresponding to the current position of the leading end of the catheter is automatically selected and displayed.

Figure 13:
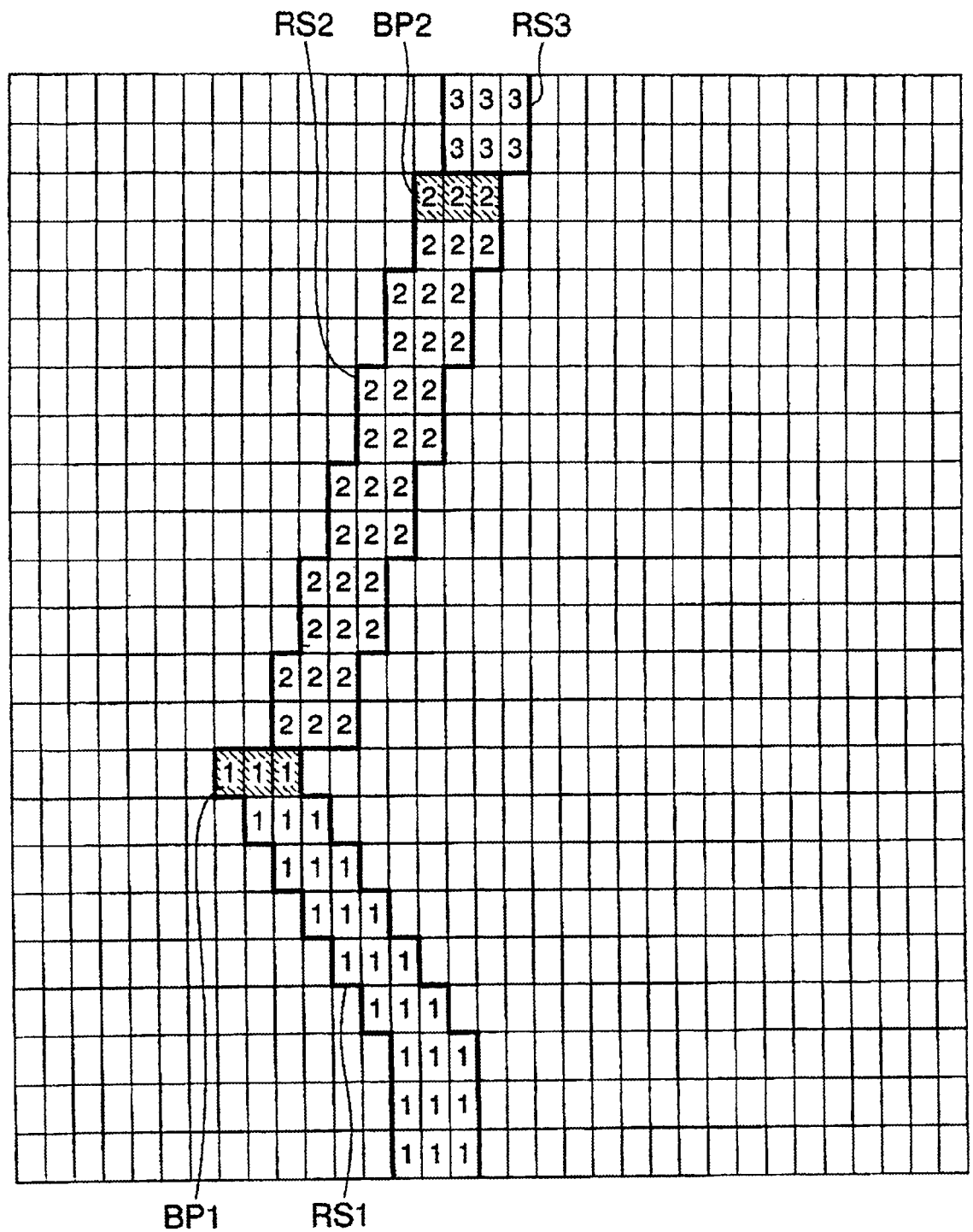
FIG. 13 is a diagram illustrating a route map generated by a route map generating process different from that shown in FIG. 4.

The process of automatically selecting and displaying the previous image is not limited to the above-mentioned method. For example, when the leading end of the catheter reaches a predetermined position on the route map, a previous image corresponding to the position of the leading end of the catheter may be searched. FIG. 13 is a diagram illustrating a route map in another automatic search and transmission process. As shown in FIG. 13, the route map generating unit 24 sets, as trigger pixels, pixels BP1 and BP2 (hatched pixels in FIG. 13) disposed on a boundary line (immediately before the next route portion) between the route portions RS1 and RS2 in another route map. When the leading end of the catheter reaches the trigger pixels BP1 and BP2, the image selecting unit 27 searches a previous image having an image number that is larger than the image numbers of the reached trigger pixels BP1 and BP2 by one. For example, when image number '1' is given to the trigger pixels (in the case of the trigger pixel BP1), a previous image having image number '2' is searched. In the above-mentioned description, the trigger pixels are disposed at the boundary between the route portions. However, the trigger pixels may be set at arbitrary positions.

When a plurality of previous images are associated with each other at the same position, for example, the images may be displayed in decreasing order of the amount of specific information (for example, the content of the procedure) included in the additional information of the corresponding image.

According to the above-mentioned structure, the image display system automatically selects an appropriate previous image corresponding to the current position of the leading end of the catheter using the route map and displays the selected previous image. Therefore, it is possible to support an IVR procedure by the physician and effectively utilize a large number of previous image data. As a result, according to this embodiment, it is possible to improve the efficiency of the IVR procedure.

The invention is not limited to the above-described embodiment, but various modifications and changes of the invention can be made without departing from the scope and spirit of the invention.

First Modification

Figure 14:
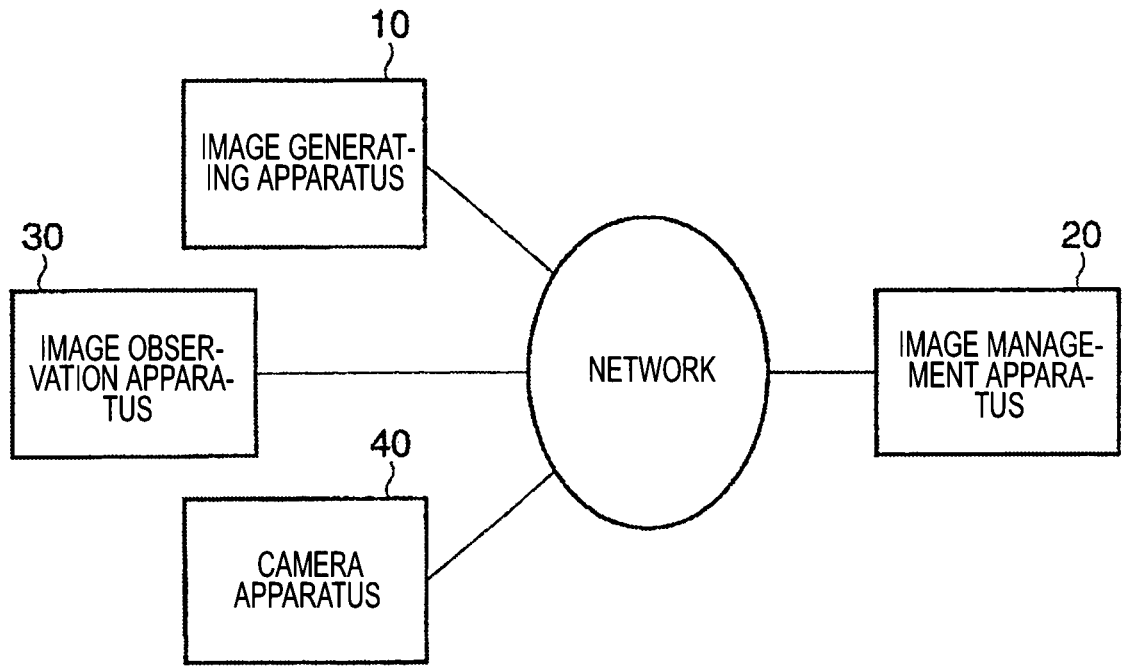
FIG. 14 is a diagram illustrating the structure of an image display system according to a first modification.

In a first modification, an example in which a capture position is not added to the image transmitted from the image generating apparatus 10 will be described. FIG. 14 is a diagram illustrating the structure of an image display system according to the first modification. As shown in FIG. 14, the image display system according to the first modification includes the image generating apparatus 10, the image management apparatus 20, the image observation apparatus 30 and a camera apparatus 40. The camera apparatus 40 is installed in an examination room. The camera apparatus 40 captures the image of the leading end of an arm (for example, an X-ray detector) of the image generating apparatus 10 that captures the current image and the image of a bed, and generates video data. The generated video data is transmitted to the image management apparatus 20. The image management apparatus 20 includes an image position calculating unit (not shown). The image position calculating unit calculates the capture position of an image on the basis of the relative positional relationship between the X-ray detector and the bed on the video data. The calculated capture position is added to the image transmitted from the image generating apparatus 10.

Figure 15:
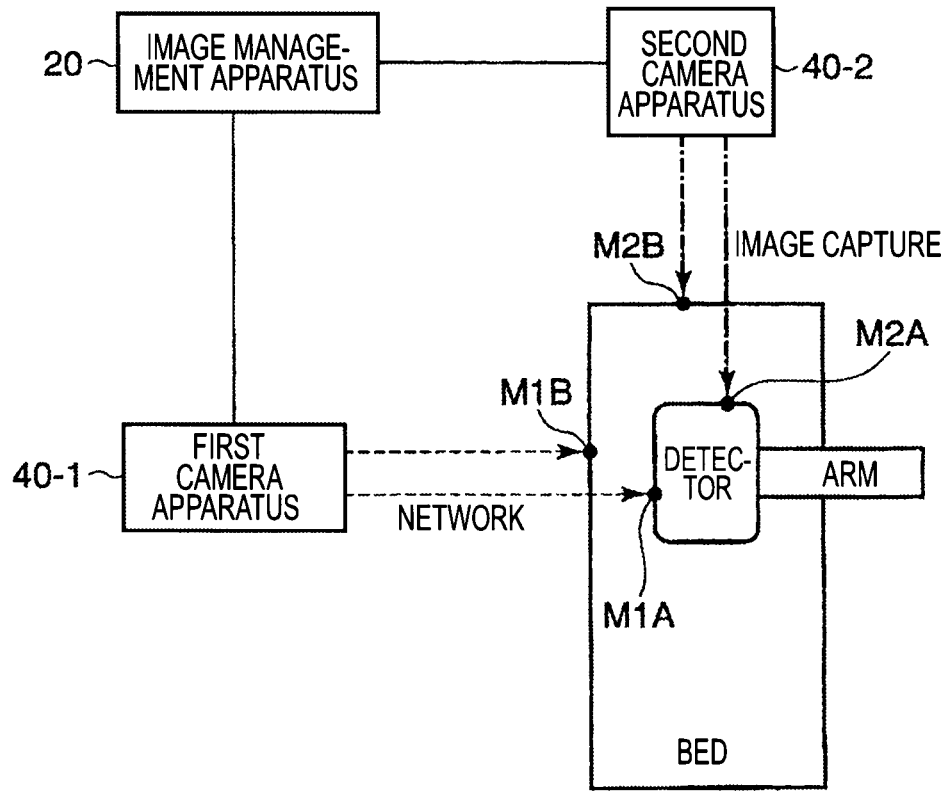
FIG. 15 is a diagram illustrating the calculation of an image capture position using a camera apparatus shown in FIG. 14.

FIG. 15 is a diagram illustrating the calculation of the capture position using the camera apparatus 40. As shown in FIG. 15, the camera apparatus 40 includes a first camera apparatus 40-1 and a second camera apparatus 40-2. The first camera apparatus 40-1 captures the image of a marker M1A attached to the X-ray detector and the image of a marker M1B attached to the bed in the lateral direction of the bed. The second camera apparatus 40-2 captures the image of a marker M2A attached to the X-ray detector and the image of a marker M2B attached to the bed in the longitudinal direction of the bed. The markers M1A, M1B, M2A, and M2B are, for example, spherical markers having a predetermined size. The image position calculating unit stores the sizes of the markers M1A, M1B, M2A, and M2B at a reference position on the images. The image position calculating unit calculates the distances between the first camera apparatus and the markers M1A and M1B on the basis of the difference between the sizes of the markers M1A and M1B at the reference position on the images and the sizes of the markers M1A and M1B at a comparative position on the images. Then, the image position calculating unit calculates the distance between the X-ray detector and the bed in the Z direction on the basis of the calculated distances. Similarly, the image position calculating unit calculates the distance between the X-ray detector and the bed in the X direction on the basis of the calculated distances.

The calculated capture position is added to an image having a capture time that is substantially the same as that of video data. Then, the same processes as described above (for example, the route map generating process shown in FIG. 4 or the automatic selection and display process shown in FIG. 11) may be performed.

In this modification, the camera apparatus 40 captures images in order to calculate the positions of the X-ray detector and the bed. However, the positions of the X-ray detector and the bed may be calculated by radiating and detecting ultrasonic waves or infrared rays, or detecting a variation in earth magnetism or magnetic flux.

According to the above-mentioned structure, even when no capture position is added to the image transmitted from the image generating apparatus 10, the image capture position is obtained by calculating the positions of the bed and the leading end (X-ray detector) of the arm, and is added to the image.

In addition, contact-type or non-contact-type displacement sensors (measuring machines: for example, an angular sensor, an inclination angle sensor, and a linear displacement sensor) may be attached to each axis of the image generating apparatus 10 and the bed, and the coordinates may be calculated by the measuring machines.

Second Modification

Figure 16:
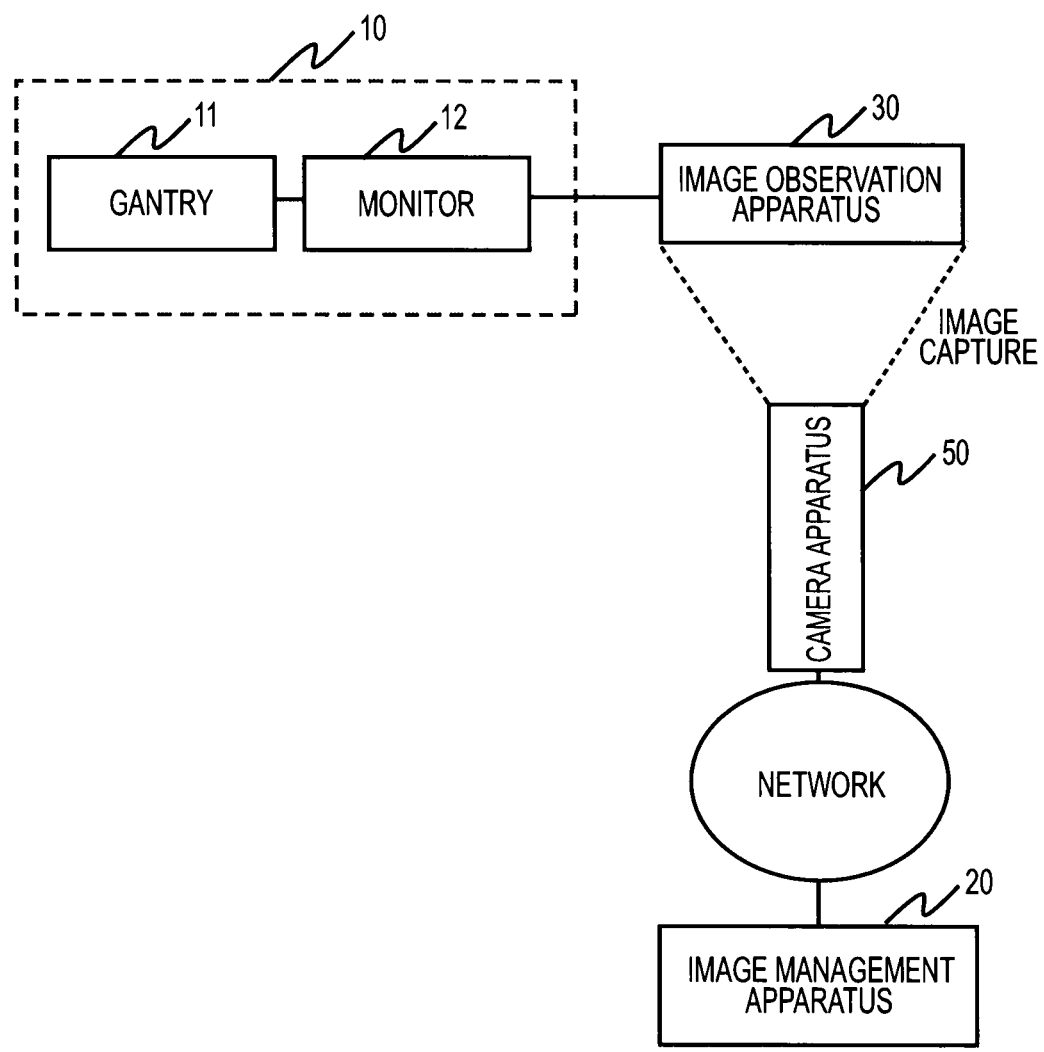
FIG. 16 is a diagram illustrating an example of the structure of an image display system according to a second modification.

In a second modification, an example in which the image management apparatus 20 cannot receive data of the current image since the data image generating apparatus 10 and the image management apparatus 20 are not connected to each other through a network, or since no image is transmitted during image capture will be described. FIG. 16 is a diagram illustrating an example of the structure of an image display system according to the second modification. As shown in FIG. 16, the image display system includes the image generating apparatus 10, the image management apparatus 20, the image observation apparatus 30, and a camera apparatus 50. The image generating apparatus 10 includes a gantry 11 and a monitor 12. The gantry 11 generates data of the current image during the current IVR procedure. The monitor 12 displays the current image. An output terminal of the monitor 12 is connected to an output terminal of the image observation apparatus 30 by a cable. The data of the current image displayed on the monitor 12 is transmitted to the image observation apparatus 30 through the cable. The image observation apparatus 30 displays the received current image on a monitor of the image observation apparatus 30. The camera apparatus 50 captures the current image displayed on the monitor of the image observation apparatus 30 and generates video data. The generated video data is transmitted as data of the current image from the camera apparatus 50 to the image management apparatus 20 through a network. Then, the same processes as described above (for example, the automatic selection and display process shown in FIG. 11) may be performed. The camera apparatus 50, the image management apparatus 20, and the image observation apparatus 30 may be connected to one another by cables. In addition, data of the previous image as well as data of the current image may be transmitted to the image management apparatus 20 by the same method as described above.

Figure 17:
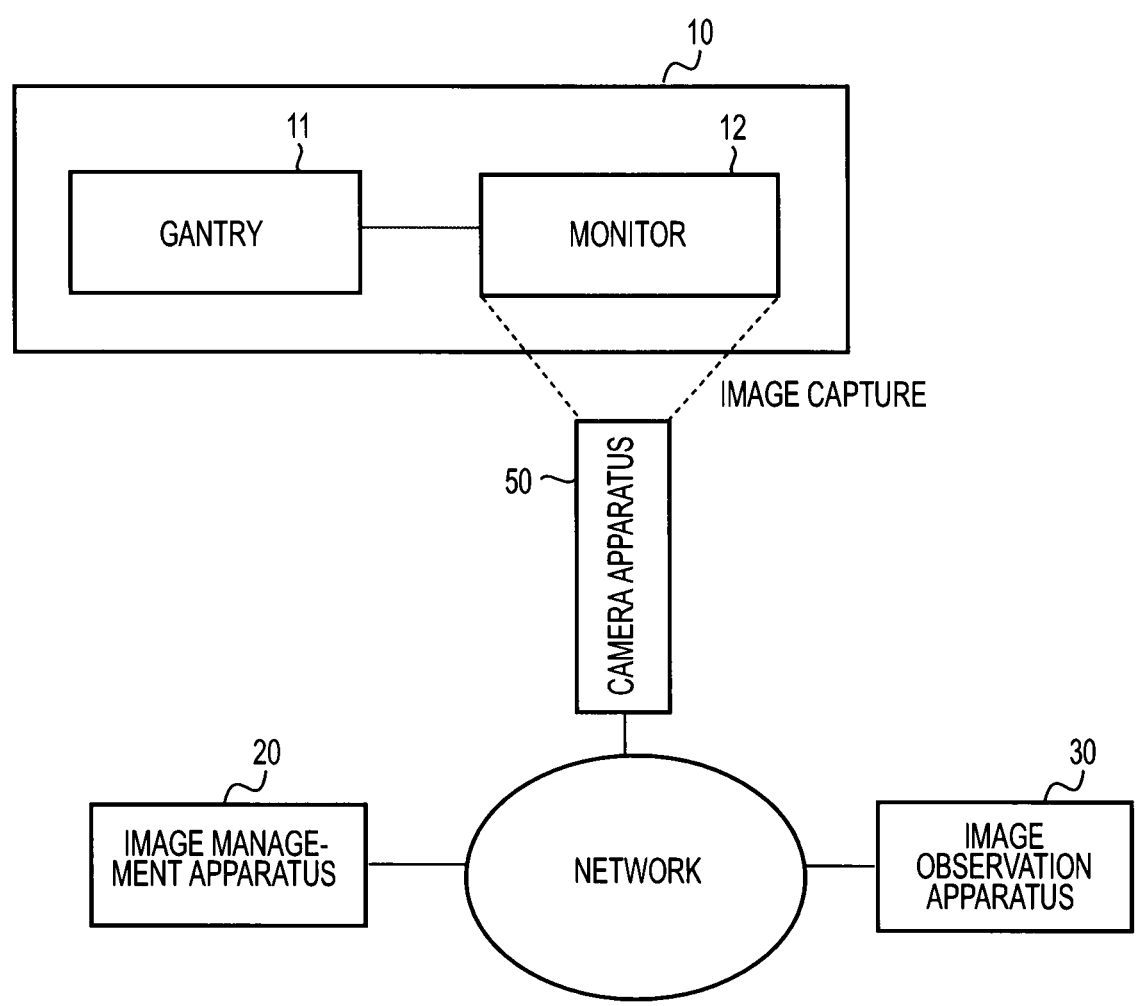
FIG. 17 is a diagram illustrating another example of the structure of the image display system according to the second modification.

FIG. 17 is a diagram illustrating another example of the structure of the image display system according to the second modification. In the image display system shown in FIG. 17, the camera apparatus 50 captures the current image displayed on the monitor 12 and generates video data. The generated video data is transmitted as data of the current image from the camera apparatus 50 to the image management apparatus 20 through a network. Then, the same processes as described above (for example, the automatic selection and display process shown in FIG. 11) may be performed. The camera apparatus 50, the image management apparatus 20, and the image observation apparatus 30 may be connected to one another by cables. In addition, data of the previous image as well as data of the current image may be transmitted to the image management apparatus 20 by the same method as described above.

Figure 18:
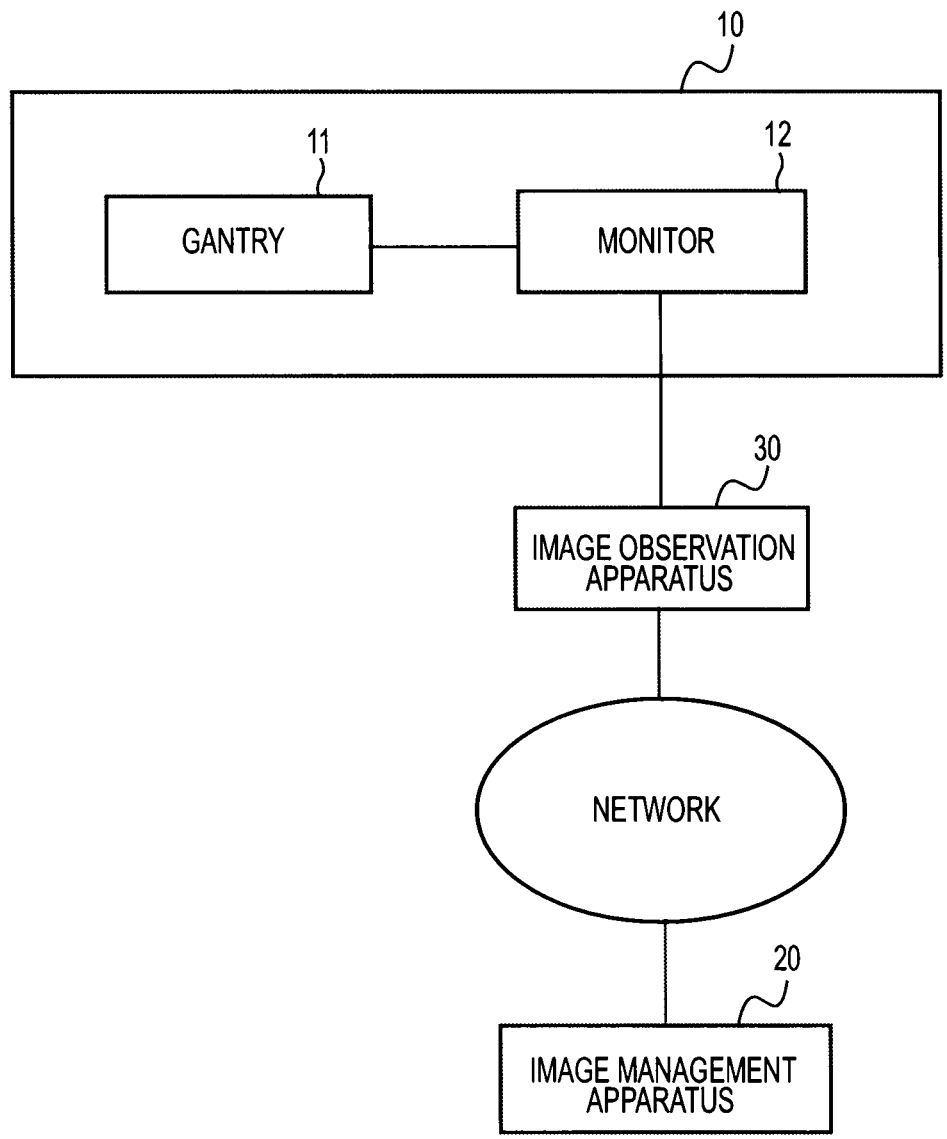
FIG. 18 is a diagram illustrating still another example of the structure of the image display system according to the second modification.

FIG. 18 is a diagram illustrating still another example of the structure of the image display system according to the second modification. The image display system shown in FIG. 18 includes the image generating apparatus 10, the image management apparatus 20, and the image observation apparatus 30. The image generating apparatus 10 includes a gantry 11 and a monitor 12. During the current IVR procedure, the gantry 11 generates data of the current image. The monitor 12 displays the current image. An output terminal of the monitor 12 is connected to an output terminal of the image observation apparatus 30 by a cable. The image generating apparatus 10 transmits data of the current image displayed on the monitor 12 to the image observation apparatus 30 through the cable. The image observation apparatus 30 displays the received current image on a monitor of the image observation apparatus 30. The image management apparatus 20 and the image observation apparatus 30 are connected to each other through a network. Data of the current image is transmitted from the image management apparatus 20 to the image observation apparatus 30 through the network. The image management apparatus 20 and the image observation apparatus 30 may be connected to each other by a cable. In addition, data of the previous image as well as data of the current image may be transmitted to the image management apparatus 20 by the same method as described above.

According to the above-mentioned structure, even when data of the current image cannot be transmitted from the image generating apparatus 10 to the image management apparatus 20, it is possible to transmit the data of the current image to the image management apparatus 20.

Third Modification

In a third modification, an example in which it is difficult to add a capture position to the current image using the methods according to the above-described embodiment and the first modification will be described. In the following description, components having substantially the same functions as those according to the above-described embodiment are denoted by the same reference numerals, and a description thereof will be made if necessary.

An image display system according to the third modification is based on the concept that the shapes of the main blood vessels of the human body are different from each other according to parts of the human body and it is possible to specify parts of the human body from the shapes of the blood vessels.

Figure 19:
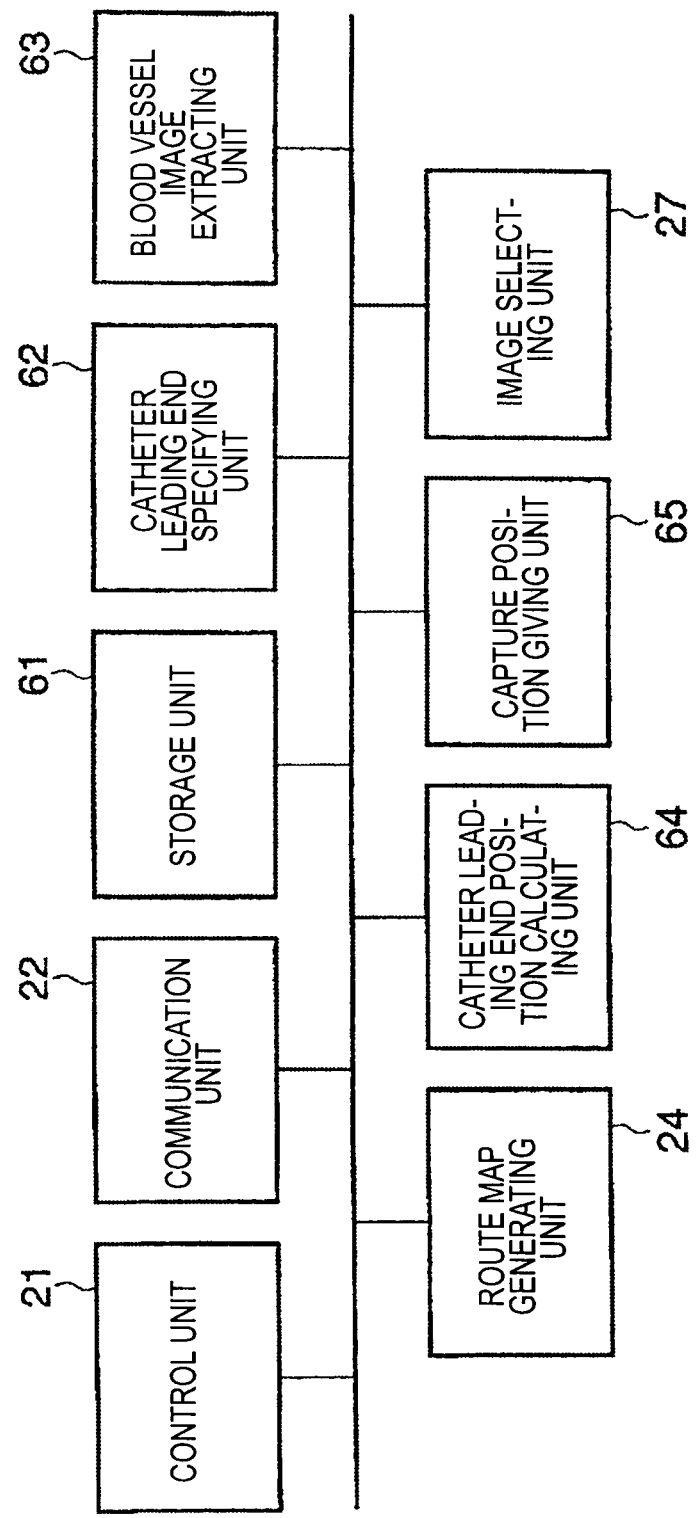
FIG. 19 is a diagram illustrating the structure of an image display system according to a third modification.

FIG. 19 is a diagram illustrating the structure of an image management apparatus 60 according to the third modification. As shown in FIG. 19, the image management apparatus 60 includes a control unit 21, a communication unit 22, a storage unit 61, a catheter leading end specifying unit 62, a blood vessel image extracting unit 63, a route map generating unit 24, a catheter leading end position calculating unit 64, a capture position giving unit 65, and an image selecting unit 27.

The storage unit 61 stores a map indicating the general shapes of the main blood vessels of the human body and the anatomical positions of the blood vessels (hereinafter, referred to as a template map). The template map is not peculiar to a patient, but is general. The template map is represented by a template map coordinate system.

The catheter leading end specifying unit 62 subtracts from a mask image a radioscopic image that is captured at the same position immediately before the mask image, thereby specifying the image of the leading end of a catheter.

The blood vessel image extracting unit 63 extracts the image of a blood vessel through which a catheter passes from the image on the basis of the position of the leading end of the catheter specified by the catheter leading end specifying unit 62.

The route map generating unit 24 arranges a plurality of catheter images included in a plurality of previous images on a route map plane according to the capture positions of the images to generate a route map.

The catheter leading end position calculating unit 64 performs a template matching process using the template map as a template and the blood vessel image as a comparative image, thereby calculating the position of the image of the blood vessel on the template map.

The capture position giving unit 65 gives the position of the image of the blood vessel on the template map as a capture position to the previous image.

Next, the capture position giving process according to the third modification will be described. A route map generating process is performed on a plurality of previous images included in one procedure image set that is stored in the storage unit 61.

Figure 20:
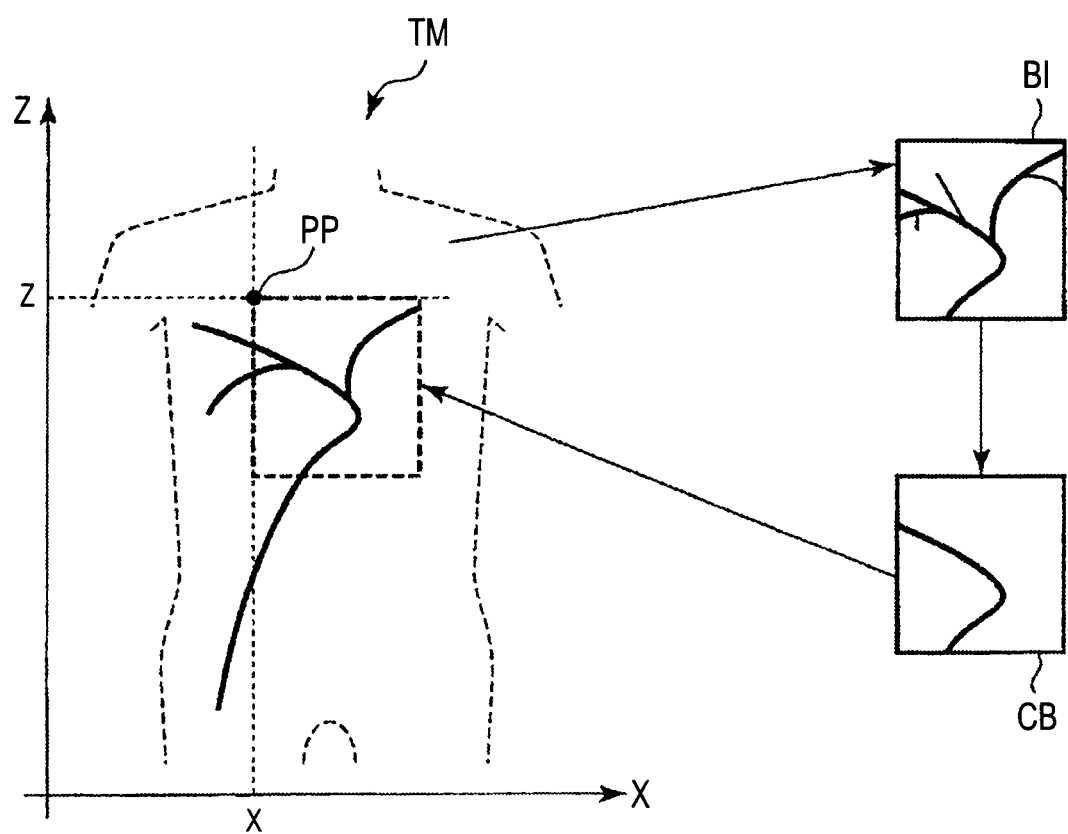
FIG. 20 is a diagram illustrating a capture position giving process according to the third modification.

FIG. 20 is a diagram illustrating the outline of the capture position giving process according to the third modification. As shown in FIG. 20, first, the image generating apparatus 10 generates data of an image BI related to the blood vessel image captured by a contrast agent. The image BI also includes a catheter image. The blood vessel image extracting unit 63 extracts the image CB of the blood vessel through which the catheter passes from the image BI, on the basis of the position of the leading end of the catheter specified by the catheter leading end specifying unit 62. The catheter leading end position calculating unit 64 performs a template matching process using a template map TM as a template and the blood vessel image BI as a comparative image, thereby specifying the position of the blood vessel image on the template map TM. When it is difficult to specify a specific part using only the shape of the blood vessel, surrounding bone images are also extracted and used for the template matching process. The capture position giving unit 65 gives the position of the blood vessel image on the template map TM as a capture position PP to the image. For example, the position of the blood vessel image on the template map is the position of the end point of the blood vessel image on the template map. When the capture position is given, the route map generating unit 24 performs processes after Step SA5 shown in FIG. 4 to generate a route map. In this case, the coordinate system of the route map is the same as that of the template map.

The process of specifying the leading end of the catheter performed by the catheter leading end specifying unit 62 is not limited to the above-mentioned method. For example, assuming that a catheter is inserted in the fixed direction, the catheter leading end specifying unit 62 may use the end point of the blood vessel image in the insertion direction as the position of the leading end of the catheter. In addition, for example, the physician may point out the position of the leading end of the catheter on the image.

According to the above-mentioned structure, even when no capture position is given to the image transmitted from the image generating apparatus 10, it is possible to use the template map to calculate the capture position of an image, and give the calculated capture position to the image.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display apparatus, comprising:
 a memory configured to store data of a plurality of previous images of a plurality of regions of a catheter generated during a previous catheter procedure, wherein the plurality of previous images are generated by performing X-ray imaging at a corresponding plurality of locations, from an insertion location of the catheter to a location of a target site;

a generating unit configured to extract a plurality of first catheter images or blood vessel images included within each of the corresponding plurality of previous images, and to generate a route map image by assigning a predetermined pixel value to those pixels in the route map image that correspond to a position of the catheter in one of the first catheter images or the blood vessel images according to a positional relationship between the plurality of regions so that the route map image indicates a combined distribution of the position of the catheter in the plurality of first catheter images or blood vessel images;

a first specifying unit configured to specify a specific portion of a current catheter image included in a current image generated during a current catheter procedure;

a first calculating unit configured to calculate a position of the specified specific portion on the route map image based on a positional relationship between the current image and the plurality of previous images; and a display configured to display a specific previous image of the plurality of previous images that corresponds to the calculated position.

2. The image display apparatus according to claim 1, wherein the generating unit is configured to allocate identification information of a previous image derived from a first catheter image or a blood vessel image to the first catheter image or the blood vessel image on the route map image, and the display is configured to display the specific previous image that is associated with identification information allocated to a first pixel of the current catheter image on the route map image or identification information allocated to a second pixel that is spaced a predetermined distance from the first pixel.

3. The image display apparatus according to claim 1, wherein, where there is a cut portion in the route map image, the generating unit is configured to interpolate the cut portion based on inclinations of two second catheter images adjacent to each other with the cut portion interposed therebetween on the route map image.

4. The image display apparatus according to claim 1, wherein the display is configured to display the route map image.

5. The image display apparatus according to claim 1, wherein the display is configured to display the route map image such that the position of the specific portion is clearly specified on the route map image.

6. The image display apparatus according to claim 1, wherein the display is configured to display the route map image such that the position of the specific previous image is clearly specified on the route map image.

7. The image display apparatus according to claim 1, further comprising:
a second calculating unit configured to calculate the position of the specific previous image or the current image based on a relative positional relationship between markers attached to a bed and markers attached to an X-ray detector.

8. The image display apparatus according to claim 1, further comprising:
a second memory configured to store data of a template map indicating shapes of main blood vessels of a human body and anatomical positions of the main blood vessels; and
a second specifying unit configured to perform a template matching process using the template map and an image of the blood vessels included in the specific previous image or the current image and to specify a position of the image of the blood vessels on the template map as the position of the specific previous image or the current image.

9. An image display system, comprising:
an image generating apparatus;
an image management apparatus; and
an image observation apparatus,
wherein the image generating apparatus includes
a current image generating unit configured to generate data of a current image during a current catheter procedure; and
a first transmitting unit configured to transmit the generated data of the current image to the image management apparatus,
wherein the image management apparatus includes
a memory configured to store data of a plurality of previous images of different regions associated with a corresponding plurality of positions generated during a previous catheter procedure, wherein the plurality of previous images are generated by performing X-ray imaging at a corresponding plurality of locations, from an insertion location of the catheter to a location of a target site;
a generating unit configured to extract a plurality of first catheter images or blood vessel images included within each of the corresponding plurality of previous images, and to generate a route map image by assigning a predetermined pixel value to those pixels in the route map image that correspond to a position of the catheter in one of the first catheter images or the blood vessel images according to a positional relationship between the plurality of regions so that the route map image indicates a combined distribution of the position of the catheter in the plurality of first catheter images or blood vessel images;
a specifying unit configured to specify a specific portion of a catheter image from the received current image;
a catheter position calculating unit configured to calculate a location of the specified specific portion on the route map image based on a capture position of the current image;
an image selecting unit configured to select a specific previous image of the plurality of previous images that corresponds to a position of the specified specific portion based on the calculated location in the route map image; and
a second transmitting unit configured to transmit the selected specific previous image to the image observation apparatus, and
the image observation apparatus includes a display configured to display the received specific previous image.

10. The image display system according to claim 9, wherein the image generating apparatus, the image management apparatus, and the image observation apparatus are connected to one another through a network.

11. The image display system according to claim 9, wherein the image generating apparatus, the image management apparatus, and the image observation apparatus are connected to one another by cables.

12. The image display system according to claim 9, wherein the image generating apparatus and the image observation apparatus are connected to each other by a cable, and
the image observation apparatus and the image management apparatus are connected to each other through a network.

13. An image display system, comprising:
an image generating apparatus;
a camera apparatus;
an image management apparatus; and
an image observation apparatus,
wherein the image generating apparatus includes
- a current image generating unit configured to generate data of a current image during a current catheter procedure; and
- a first display configured to display the generated current image, wherein the camera apparatus captures an image of the displayed current image to generate video data, and transmits the generated video data, to the image management apparatus, the image management apparatus includes
- a memory configured to store data of a plurality of previous images of different regions associated with a corresponding plurality of positions generated during a previous catheter procedure, wherein the plurality of previous images are generated by performing X-ray imaging at a corresponding plurality of locations, from an insertion location of the catheter to a location of a target site;
- a generating unit configured to extract a plurality of first catheter images or blood vessel images included within each of the corresponding plurality of previous images, and to generate a route map image by assigning a predetermined pixel value to those pixels in the route map image that correspond to a position of the catheter in one of the first catheter images or the blood vessel images according to a positional relationship between the plurality of regions so that the route map image indicates a combined distribution of the position of the catheter in the plurality of first catheter images or blood vessel images;
- a specifying unit configured to specify a specific portion of a catheter image from the received video data;
- a catheter position calculating unit configured to calculate a location of the specified specific portion on the route map image based on a capture position of the current image;
- an image selecting unit configured to select a specific previous image of the plurality of previous images that corresponds to a position of the specified specific portion based on the calculated location in the route map image; and
- a second transmitting unit configured to transmit the selected specific previous image to the image observation apparatus, and the image observation apparatus includes a second display configured to display the received specific previous image.

14. The image display system of claim 9,
wherein the catheter position calculating unit is configured to calculated a pixel location as the location of the specified specific portion on the route map.

15. The image display system of claim 13,
wherein the catheter position calculating unit is configured to calculated a pixel location as the location of the specified specific portion on the route map.

* * * * *